US011566234B2

(12) United States Patent
Marquette et al.

(10) Patent No.: US 11,566,234 B2
(45) Date of Patent: Jan. 31, 2023

(54) METHOD FOR MANUFACTURING BODY SUBSTITUTES BY ADDITIVE DEPOSITION

(71) Applicants: Lab Skin Creations, Lyons (FR); Universite Claude Bernard Lyon 1, Villeurbanne (FR); Centre National de la Recherche Scientifique, Paris (FR); Institut National des Sciences Appliquees de Lyon, Villeurbanne (FR); Ecole Superieure de Chimie, Physique, Electronique de Lyon, Villeurbanne (FR)

(72) Inventors: Christophe Marquette, Villeurbanne (FR); Léa Pourchet, Lyons (FR); Amélie Thepot, Lyons (FR); Morgan Dos Santos, Saint Verand (FR)

(73) Assignees: LAB SKIN CREATIONS, Lyons (FR); UNIVERSITE CLAUDE BERNARD LYON 1, Villeurbanne (FR); CENTRE NATIONAL DE LA RECHERCHE SCIENTIFIQUE, Paris (FR); INSTITUT NATIONAL DES SCIENCES APPLIQUEES DE LYON, Villeurbanne (FR); ECOLE SUPERIEURE DE CHIMIE, PHYSIQUE, ELECTRONIQUE DE LYON, Villeurbanne (FR)

(*) Notice: Subject to any disclaimer, the term of this patent is extended or adjusted under 35 U.S.C. 154(b) by 569 days.

(21) Appl. No.: 16/064,322

(22) PCT Filed: Dec. 29, 2016

(86) PCT No.: PCT/FR2016/053683
§ 371 (c)(1),
(2) Date: Jun. 20, 2018

(87) PCT Pub. No.: WO2017/115056
PCT Pub. Date: Jul. 6, 2017

(65) Prior Publication Data
US 2019/0002836 A1    Jan. 3, 2019

(30) Foreign Application Priority Data

Dec. 30, 2015  (FR) ...................................... 1563461
Mar. 3, 2016   (FR) ...................................... 1651797

(51) Int. Cl.
| | |
|---|---|
| *C12N 5/071* | (2010.01) |
| *B33Y 70/00* | (2020.01) |
| *B33Y 80/00* | (2015.01) |
| *G01N 33/50* | (2006.01) |
| *B33Y 10/00* | (2015.01) |
| *A61L 27/38* | (2006.01) |
| *C12N 5/077* | (2010.01) |

(52) U.S. Cl.
CPC ........ *C12N 5/0698* (2013.01); *A61L 27/3843* (2013.01); *B33Y 10/00* (2014.12); *B33Y 70/00* (2014.12); *B33Y 80/00* (2014.12); *C12N 5/0629* (2013.01); *C12N 5/0656* (2013.01); *G01N 33/50* (2013.01); *C12N 2500/38* (2013.01); *C12N 2501/11* (2013.01); *C12N 2501/33* (2013.01); *C12N 2501/39* (2013.01); *C12N 2501/395* (2013.01); *C12N 2501/805* (2013.01); *C12N 2502/091* (2013.01); *C12N 2502/092* (2013.01); *C12N 2502/094* (2013.01); *C12N 2502/097* (2013.01); *C12N 2502/1305* (2013.01); *C12N 2502/1323* (2013.01); *C12N 2503/06* (2013.01); *C12N 2533/30* (2013.01); *C12N 2533/52* (2013.01); *C12N 2533/54* (2013.01); *C12N 2533/56* (2013.01); *C12N 2533/74* (2013.01)

(58) Field of Classification Search
CPC .. C12N 5/0698; C12N 5/0629; C12N 5/0656; C12N 5/098; B33Y 10/00; B33Y 70/00; B33Y 80/00; A61L 27/3843; G01N 33/50
See application file for complete search history.

(56) References Cited

FOREIGN PATENT DOCUMENTS

| | | |
|---|---|---|
| JP | 2003-533367 A | 11/2003 |
| JP | 2009207963 A | 9/2009 |
| WO | 2012153815 A1 | 11/2012 |

OTHER PUBLICATIONS

Zhao et al., "Three-dimensional printing of Hela cells for cervical tumor model in vitro", 2014, Biofabrication 6, p. 1-10.*

(Continued)

*Primary Examiner* — Scott Long
(74) *Attorney, Agent, or Firm* — Jordan IP Law, LLC; Todd A. Vaughn

(57) ABSTRACT

The invention relates to a method for manufacturing a bio-ink by additive deposition, which comprises supplying: a first solution including between 5 and 40 wt. % gelatin; a second solution including between 15 and 35.wt. % alginate; a third solution including between 1 and 15 wt. % fibrinogen, and optionally living cells in suspension; and creating a mixture including: around 35 to 65 vol. % of the first solution; around 15 to 35 vol. % of the second solution; and around 15 to 35 vol. % of the third solution, said proportions being selected so that they add up to 100%. Said bio-ink allows the additive deposition of objects that can be polymerised by means of a solution including calcium ions and thrombin. Said objects can be incubated and can be used as a substitute for body tissue, for example (with added fibroblasts) as skin substitute.

25 Claims, 12 Drawing Sheets

(56) References Cited

OTHER PUBLICATIONS

Li et al., "Direct Fabrication of a Hybrid Cell/Hydrogel Construct by a Double-nozzle Assembling Technology", 2009, Journal of Bioactive and Compatible Polymers 24, p. 249-265.*

Zhao et al., "Three-dimensional printing of Hela cells for cervical tumor model in vitro", Apr. 11, 2014, Biofabrication 6, p. 1-10.*

Huang et al., "Rapid prototyping of a hybrid hierarchical polyurethane-cell/hydrogel construct for regenerative medicine", 2013, Materials Science and Engineering C 33, p. 3220-3229.*

Sui et al., "Cryopreservation of Cells in 3D Constructs Based on Controlled Cell Assembly Processes", 2009, Journal of Bioactive and Compatible Polymers 24, p. 473-487.*

He et al., Rapid prototyping of tubular polyurethane and cell/hydrogel constructs:, 2011, Journal of Bioactive and Compatible Polymers 26(4), p. 363-374.*

Trottier et al., "IFATS Collection: Using Human Adipose-Derived Stem/Stromal Cells for the Production of New Skin Substitutes", 2008, Stem Cells 26, p. 2713-2723.*

Li et al., "Direct Fabrication of a Hybrid Cell/Hydrogel Construct by a Double-nozzle Assembling Technology", Journal of Bioactive and Compatible Polymers, May 2009, vol. 24, No. 3, pp. 249-265.

Huang et al., "Rapid prototyping of a hybrid hierarchical polyurethane-cell/hydrogel construct for regenerative medicine", Materials Science and Engineering: C, Apr. 6, 2013, vol. 33, No. 6, pp. 3220-3229.

Zhao et al., "Three-dimensional printing of Hela cells for cervical tumor model in vitro", Biofabrication, Apr. 11, 2014, vol. 6, No. 3, 10 pages.

Lee et al., "Design and Fabrication of Human Skin by Three-Dimensional Bioprinting", Tissue Engineering: C, Jun. 2014, vol. 20, No. 6, pp. 473-484.

Dai et al., "3D bioprinted glioma stem cells for brain tumor model and applications of drug susceptibility", Biofabrication, Oct. 11, 2016, vol. 8, No. 4, pp. 1-11.

\* cited by examiner

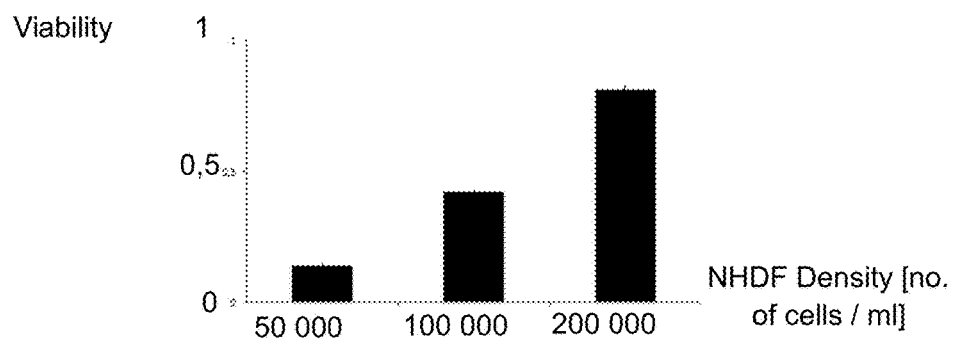
Figure 5(a)
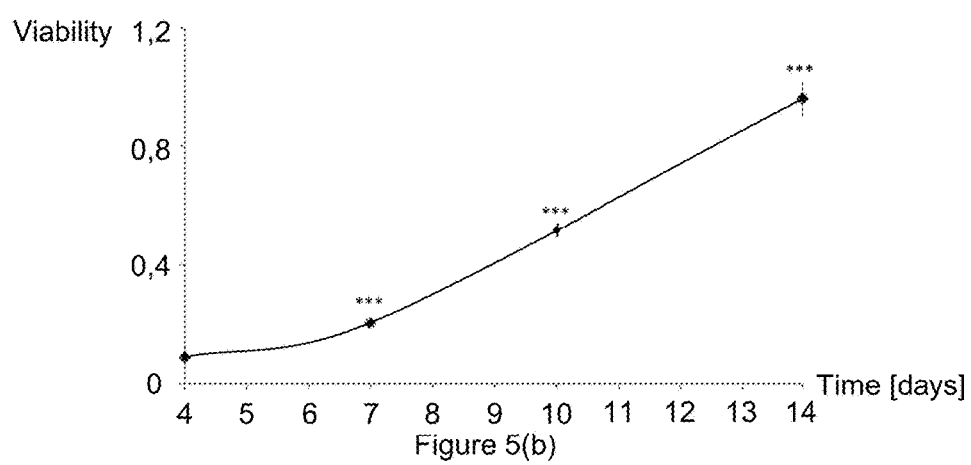
Figure 5(b)
 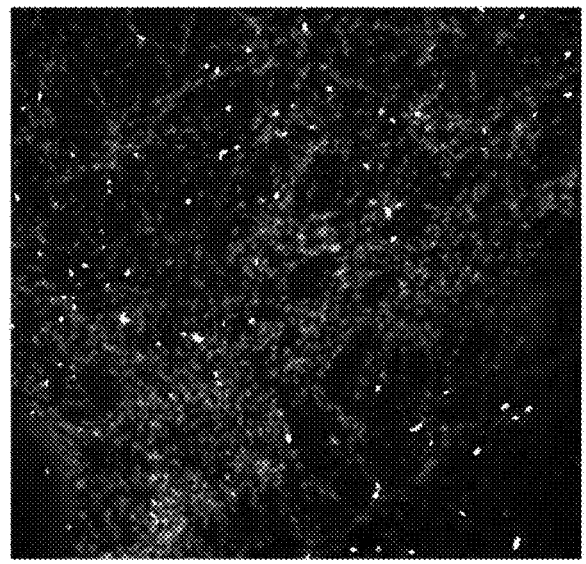
Figure (5c)　　　　　　　　　　　Figure 5(d)

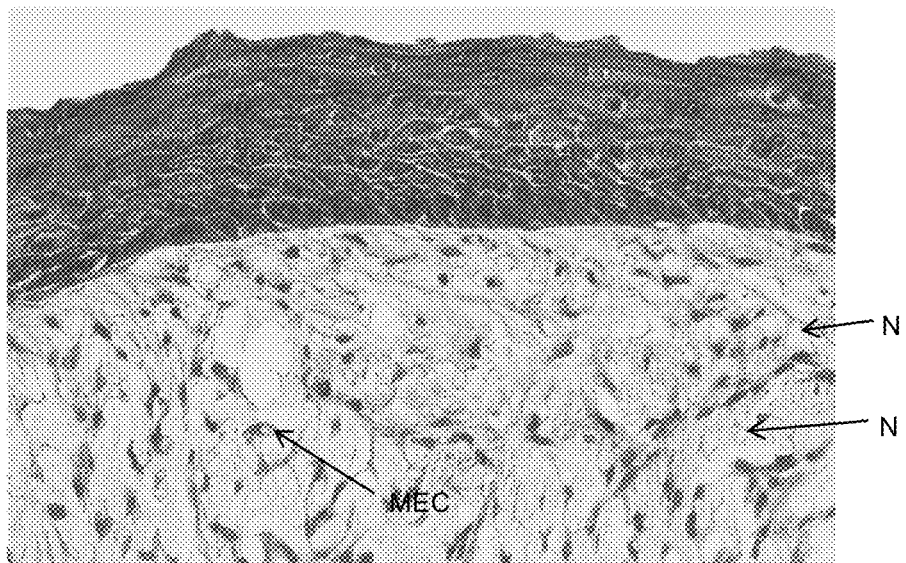
Figure 7(b)
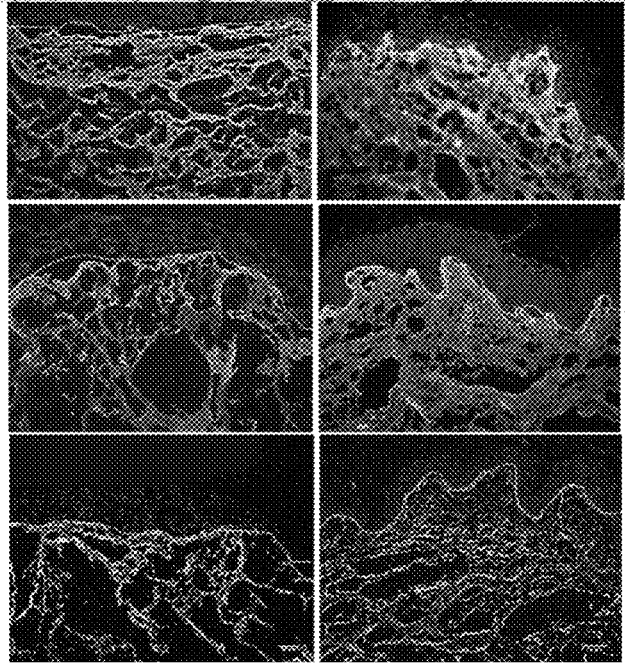
Figure 7(c)
Figure 7(d)
Figure 7(e)
Figure 7(f)
Figure 7(g)
Figure 7(h)
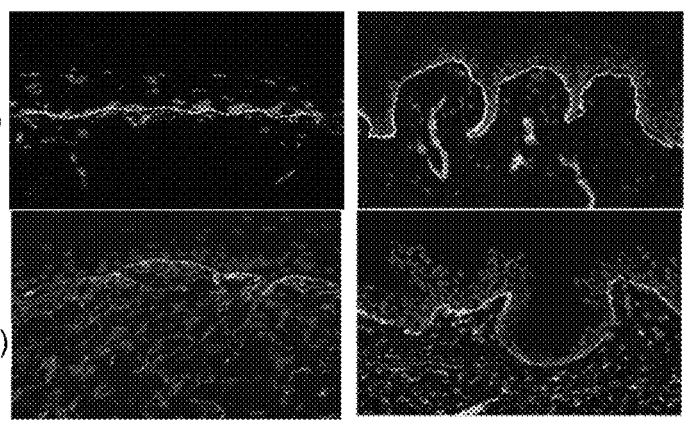
Figure 7(i)
Figure 7(j)
Figure 7(k)
Figure 7(l)

Figure 10(b)
Figure 10(c)
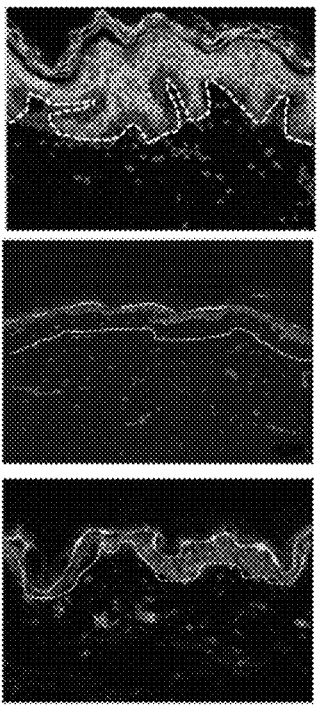
Figure 10(d)
Figure 10(e)
Figure 10(f)
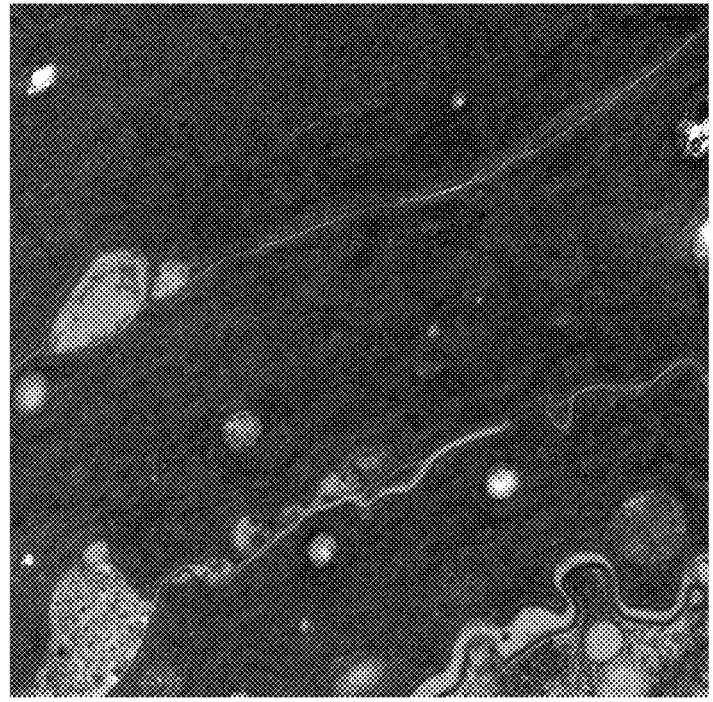
Figure 11(a)

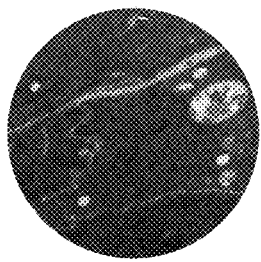
Figure 11(b)
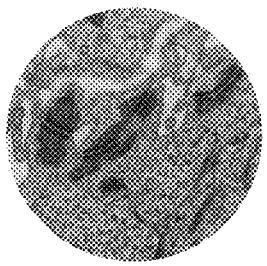
Figure 11(c)
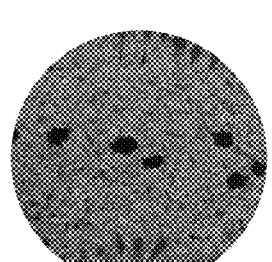
Figure 11(d)
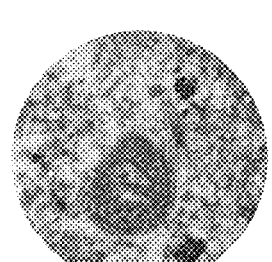
Figure 11(e)
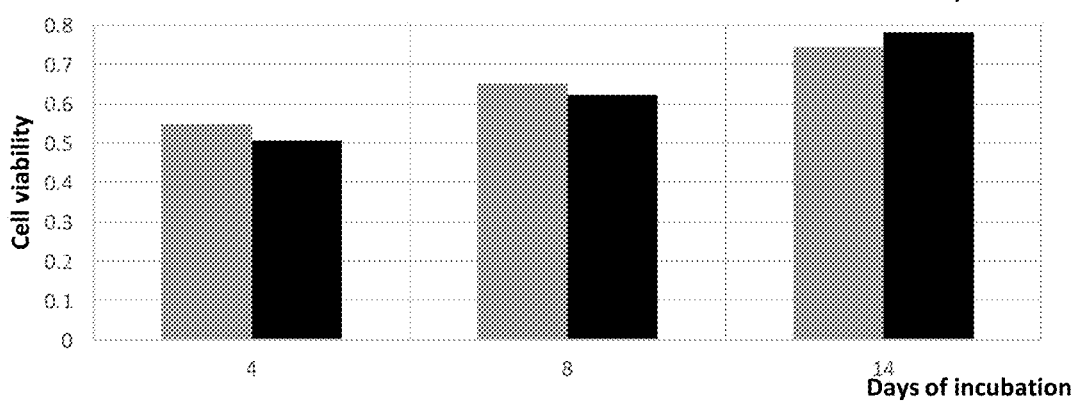
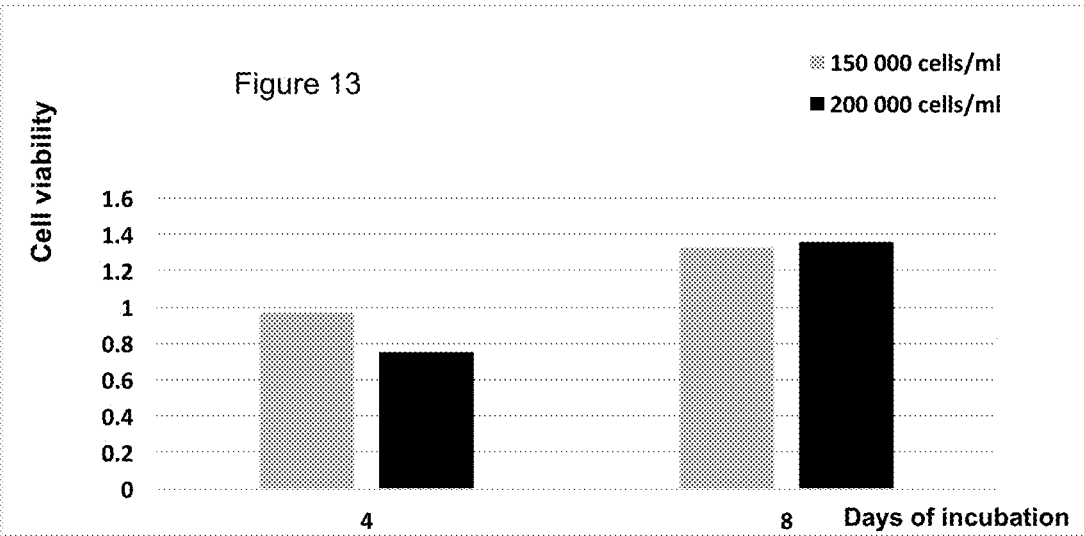

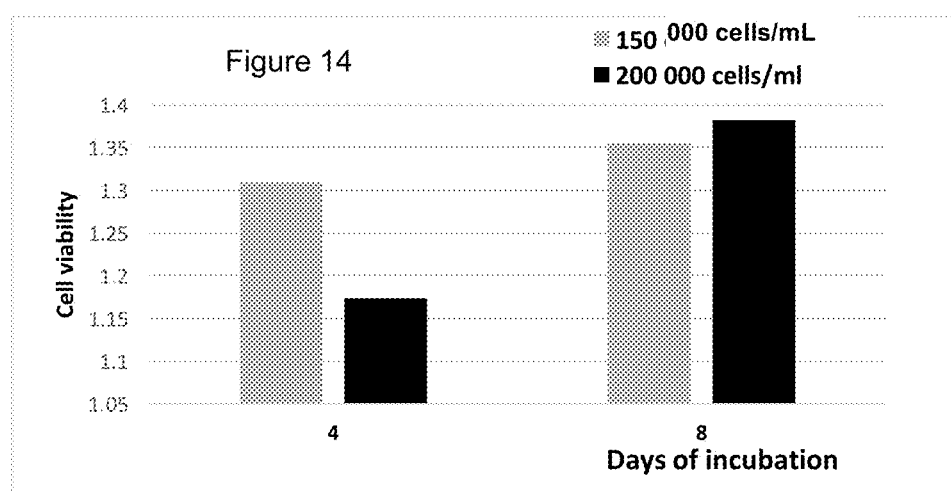
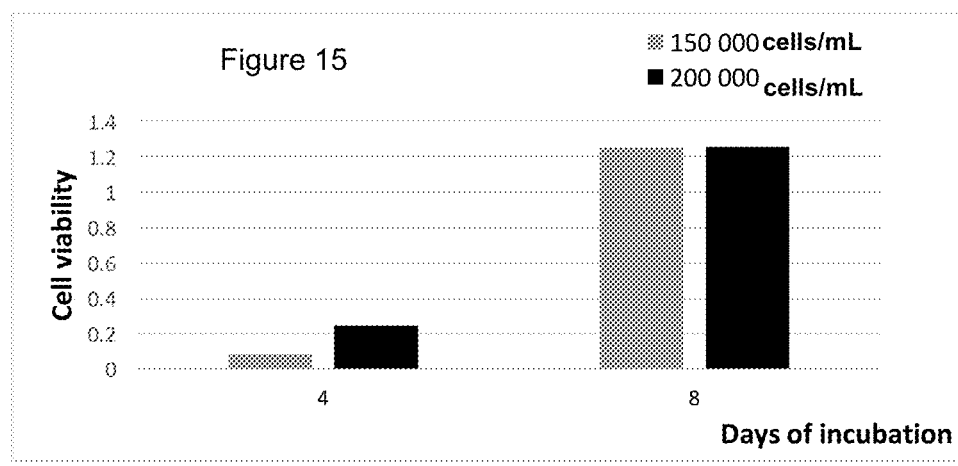

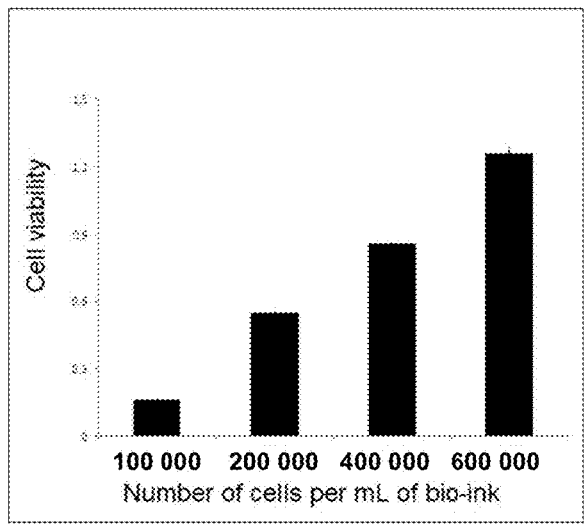
Figure 16(a)
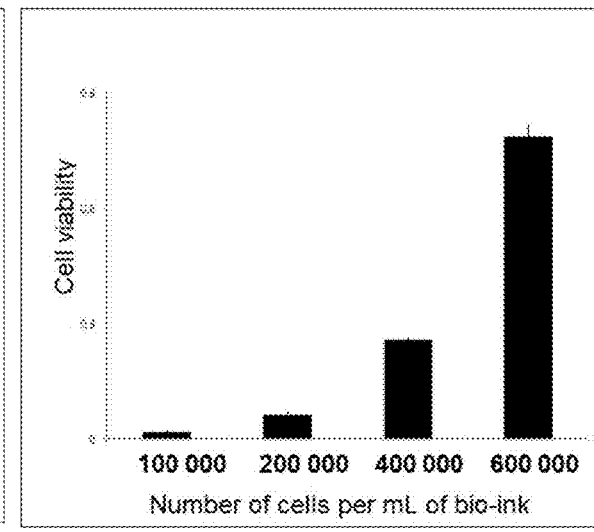
Figure 16(b)
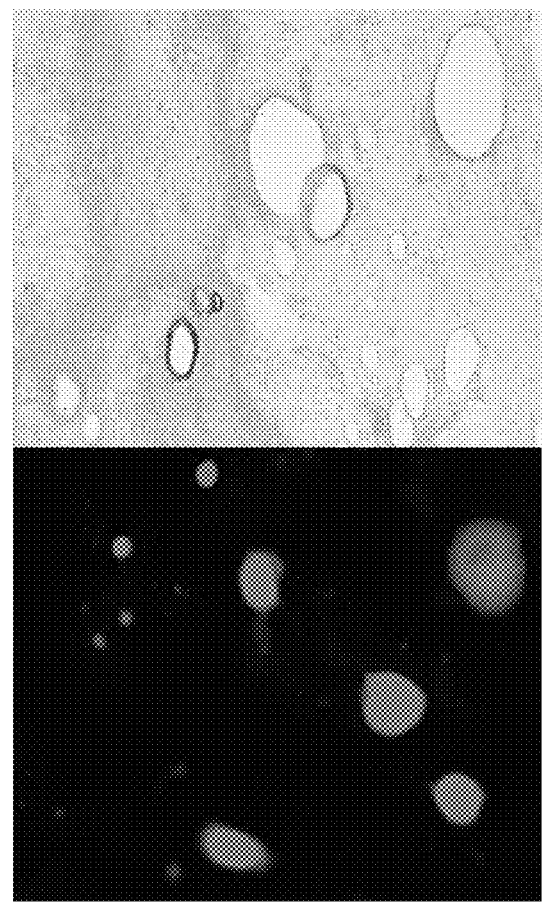
Figure 16(c)
Figure 16(d)

METHOD FOR MANUFACTURING BODY SUBSTITUTES BY ADDITIVE DEPOSITION

CROSS-REFERENCE TO RELATED APPLICATIONS

The present application is a National Stage Application of PCT International Application No. PCT/FR2016/053683 (filed on Dec. 29, 2016), under 35 U.S.C. § 371, which claims priority to French Patent Application Nos. 1563461 (filed on Dec. 30, 2015) and 1651797 (filed on Mar. 3, 2016), which are each hereby incorporated by reference in their respective entireties.

TECHNICAL FIELD

The invention relates to the field of biotechnology and more particularly body tissue substitutes, especially substitutes for skin tissues. In particular it relates to the fabrication of body substitutes (such as skin) intended to be implanted in the body or the performance of tests on pharmaceutical or cosmetic active constituents to evaluate their toxicity, their efficiency or penetration in the body tissue.

STATE OF PRIOR ART

In Europe, chemical products for use in cosmetics can no longer be tested on laboratory animals; therefore continuous attempts are made to improve skin substitutes, to confer characteristics on them more closely resembling the characteristics of a natural dermis, to reduce their production and usage cost. Among the different experimental methods for fabricating biotechnological materials and matrices, additive deposition methods have received considerable attention during the last few years.

Initially designed for fabricating model industrial parts made of plastic (fast prototyping, see FR 2 567 668), additive fabrication methods, some of which are known under the terms "stereolithography" or "3D printing" have been explored in many application fields during approximately the last decade. They generally comprise the deposition of a powder, paste or liquid (ink) phase in a controlled three-dimensional form on an initial substrate, followed by solidification of this deposited phase to obtain an object with a controlled three-dimensional shape. Said deposit is usually made in several passes each leading to the deposition of a powder, paste or liquid phase in a controlled three-dimensional form; these depositions are traditionally solidified pass by pass (stratum by stratum). Said powder, paste or liquid phase may be homogeneous (for example a homogeneous powder or a molten thermoplastic polymer) or may comprise a dispersion of solid particles in a liquid phase. Its viscosity may be a critical parameter because the preform obtained after its deposition must not collapse while waiting for its solidification (this waiting time may be a fraction of a second). It may be solidified by very different techniques depending on the composition of the ink; it may also take place spontaneously, particularly in the case of an extruded polymer in the molten state that solidifies, or in the case of thixotropic pastes or in the case of a polymer with a composition that comprises molecules that react with each other (as is described in U.S. Pat. No. 6,942,830).

For example, plastic parts can be fabricated by depositing an ink that can be polymerized by light (or by the heat generated by absorption) of a laser beam, and metallic parts can be fabricated by depositing pastes containing metallic particles or powders that are consolidated (usually by intermediate melting) under the effect of a laser beam (technique known as SLS (Selective Laser Sintering); molten metals can also be deposited directly. Complex shaped industrial parts can thus be fabricated. There is a large number of techniques (and abbreviations referring to them) on the market, such as FDM™ (Fused Deposition Modeling), multiple jet modelling and FTI (Film Transfer Imaging). The abbreviation SFF (Solid Freeform Fabrication) is used to designate a set of techniques that can be used to fabricate three-dimensional structures directly from CAD (Computer-Aided Design) files using additive techniques.

The use of addition fabrication techniques is known in prior art in the biotechnology field; thus, three-dimensional structures based on "biological" materials have been printed. More precisely, in this the case the inks used are biocompatible materials capable of solidifying. These materials can be used as a scaffold for living cells that are introduced after the scaffold has solidified. Living cells can also be introduced into the ink directly that is then a suspension containing living cells; these inks are sometimes called "bio-inks".

This solidification can be done by a photochemical method. For example, document US 2014/0052285 describes the use of several types of photopolymerizable hydrogels, namely PEG-DA (=polyethylene glycol diacrylate), PEG-DA-PEA (polyester amide), GMA-chitosan and alginate, to make scaffolds capable of being colonized by living cells. US 2013/0304233 describes the fabrication of resorbable scaffold structures based on PPF (polypropylene fumarate). U.S. Pat. Nos. 7,780,897 and 8,197,743 describe other embodiments of stereolithography using polyethylene glycol hydrogels solidified by a photochemical reaction. However, solidification by photochemistry requires significant quantities of photocatalysts, photoinitiators and/or stains (for example: 2% photoinitiator); these additives can create a toxicological problem. Concerning the photocatalyst, even if it is not toxic in itself, the production of free radicals is always conducive to cell mortality and a risk of disturbing the product obtained. This is why it is required to find an alternative to photopolymerization for biotechnological applications.

Hydrogels have also been used in the past as a solidifiable paste medium; U.S. Pat. No. 7,051,654 describes a very long list of them. US 2014/003932 describes photocure hydrogels based on methacrylate. US 2014/0012407 more specifically describes thermoreversible hydrogels. EP 2 670 669 A1 describes a method in which a suspension of living cells is deposited comprising a first hydrogel precursor capable of solidifying when the temperature drops below a critical gelling temperature, and a second cross-linkable hydrogen precursor, the deposited suspension is solidified by cooling it, and a curing agent is added. The second precursor can be an alginate, hyaluronic acid, a cellulose derivative, chitosan, xanthan, fibrin, a pectin gel, or polyvinyl alcohol. In general, solidified hydrogels for a cell culture scaffold are known to a person skilled in the art under the name "lattice". Other solidifiable systems are described in US 2013/0164339 and US 2014/00998709.

Alginate based inks are also known that are solidified with a solution to fabricate scaffolds for cell culture; such systems and methods are described in U.S. Pat. Nos. 8,639,484, 8,691,974 and 8,691,274.

US 2013/0017564 describes the hydroxyapatite deposit to make three-dimensional structures on which bone cells, osteoblasts, can be deposited.

3D printing was also used in biotechnology to apply ink containing living cells onto a scaffold conducive to the development of cell cultures. US 2009/0208466 and WO 2014/039427 describe 3D printing with inks based on collagen (that can comprise alginate) containing human cells. US 2011/0250688 describes the deposition of smooth muscle cells suspended in a hydrogel by 3D printing on a biological or synthetic support.

US 2012/0089238 describes the deposition of four different cell types on a porous substrate (scaffold) by 3D printing, each deposited in suspension starting from a dedicated print head, to create a complex three-dimensional structure miming a tissue. WO 2013/040087 describes the fabrication of "lattice" type biocompatible structures by 3D printing onto which living tissues characteristic of a certain range of tissues have been fixed; smooth muscle cells, dermal fibroblasts, endothelial cells, hepatic stellate cells), hepatocytes, monocytes, macrophages. The publication entitled "Multilayered culture of human skin fibroblasts and keratinocytes through three-dimensional freeform fabrication" by W. Lee et al., published in the journal Biomaterials 30 (2009), p. 1587-1595, describes the deposition by 3D printing of cells on a type I collagen based hydrogel lattice, deposited in the same manner. In particular, this publication describes the fabrication of multi-layer collagen structures in which some layers incorporate fibroblasts or keratinocytes; after incubation of the cells they can be used as a skin model.

The publication entitled "On-Demand Three-Dimensional Freeform Fabrication of Multi-Layered Hydrogel Scaffold With Fluidic Channels" by W. Lee et al., published in 2010 in the journal Biotechnology and Bioengineering, vol. 105 (6), p. 1178-1186, describes a method of depositing a biomaterial from alternating layers of a collagen-based hydrogel and a gelatin solution; the hydrogel is cross-linked with sodium bicarbonate, while the gelatin solution solidifies by cooling during deposition. The cells to be cultivated are contained in the collagen hydrogel. During incubation, the gelatin solution becomes liquid and is removed by rinsing; the result is that a structure is creating comprising dense layers of collagen hydrogel alternating with slightly dense layers left by the departure of gelatin. Although this biomaterial can be used for the culture of cells, it is not a skin substitute.

The publication entitled "Design and Fabrication of Human Skin by Three-Dimensional Bioprinting" by V. Lee et al., published in the journal Tissue Engineering Part C, 20(6) (2014), p. 473-484, shows that multilayer systems obtained by manual assembly and by 3D printing develop very differently under cell culture conditions: systems created by 3D printing thrive and maintain their shape, while systems assembled manually wither away.

At the present time, most 3D printed products in biotechnology result in products that can be used as models for scientific studies; a large variety of cells and organs can be mimed in this manner. The model systems can be used to characterize pharmaceutical active constituents on cell cultures raised and maintained under conditions similar to intracorporal conditions. The publication entitled "Three-dimensional printing of Hela cells for cervical tumor model in vitro" by Y. Zhao et al., published in the journal Biofabrication 6 (1914), doi:10.1088/1758-5082/6/3/035001, offers an example.

On the other hand, and still in the field of human skin, the therapeutic stakes are enormous because there are still many unsatisfied needs. Thus, document US 2014/0012225 describes a device for depositing solidifiable hydrogels comprising epidermal cells as artificial skin, on extensive zones of the surface of the human body; this device was designed for the treatment of severe burns.

This invention relates to the field of body substitutes, and particularly skin substitutes, intended either to be implanted in the body, or for performing tests on pharmaceutical or cosmetic active constituents. The inventors have observed that traditional methods for fabricating body substitutes, and particularly skin substitutes, take a long time in two respects; firstly they require a long manipulation time (expressed in man-hours) because the fabrication of body substitutes and particularly skin substitutes is a complex process; and secondly the porous substrate (scaffold) necessary for the fabrication of skin substitutes cannot be used as such but must firstly be allowed to age for several months (typically about six months) before it can be used under culture conditions. The culture phase itself takes at least six to seven weeks. It should also be noted that the complex manipulation during fabrication implies a risk of contamination of cultures.

Techniques for the fabrication of skin substitutes from a bio-ink can easily be automated, their reproducibility is good and they can thus be used to obtain a normalized product and they are faster: the biomaterial is mixed with cells on the day of production to form bio-ink, and the dermis matures in ten to fifteen days.

However, the result is not very good because we do not obtain an artificial dermis usable for the culture of a stratified epidermis on its surface, that can be used as a realistic model of a natural skin. The publication entitled "Standardized 3D Bioprinting of Soft Tissue Models with Human Primary Cells" by M. Riemann et al., published in 2015 in J. of Laboratory Automation, p. 1-14 (doi: 10.1177/2211068214567146) describes the fabrication of a skin substitute by the additive deposition of successive layers (individual thickness: 0.05 mm) of a photopolymerizable bio-ink; a matrix layer is alternated with a layer comprising fibroblasts. This layer is immediately photopolymerized. The bio-ink is based on PEG. However, the skin substitute thus obtained does not have the stratified structure of a natural epidermis, and it contains many holes.

At the present time, there is no solution to the problem de fabricating a skin substitute with a sufficient structural and functional resemblance to natural skin, using additive techniques.

Purpose of the Invention

The problem is solved according to the invention by using a new composition of bio-ink comprising a mixture of natural gelatin, alginate and fibrinogen that is solidified by three different means: during deposition of the ink, the gelatin solidifies by cooling so that the bead shape of the deposited ink can be maintained. After deposition, the deposited object is treated with a solution containing calcium ions and thrombin, to solidify the alginate by calcium ions and to coagulate fibrinogen by the thrombin effect.

Thus, a first subject-matter of the invention is a method of fabricating a bio-ink for additive deposition, in which:

(a) A first solution is provided containing between 5% and 40% by mass of gelatin (preferably between 6% and 30% by mass) and between 0% and 5% by mass of NaCl;

(b) A second solution is provided containing between 1% and 12% by mass of alginate (preferably between 1% and 8% by mass) and between 0% and 5% by mass of NaCl;

(c) A third solution is provided containing between 1% and 15% by mass of fibrinogen (preferably between 3% and 15% by mass) and optionally living cells (such as fibroblasts) in suspension;

(d) A mixture is created containing:
about 35% to 65% by volume of the first solution; about 15% to 35% by volume of the second solution; about 15% to 35% by volume of the third solution; these proportions being chosen to add up to 100%,
and in which method:
the order of steps (a), (b) and (c) is indifferent,
the NaCl content is chosen such that in said first solution and said second solution combined, it is between 0.2% and 5% by mass, preferably between 0.2 and 3% by mass, and even more preferably between 0.4% and 2% by mass.

For the preparation of skin substitutes, said living cells can be derived from different structures of the skin: dermis, epidermis, hypodermis, blood and lymph vessels, hair follicle, sebaceous glands, sweat glands, pores, hair erection muscles, muscles, Meissner's corpuscles, Pacini's corpuscles, Ruffini's corpuscles, connective tissue, basal membrane. More particularly, these cells may be keratinocytes, melanocytes (particularly phototypes I, II, III, IV and V according to the Fitzpatrick scale), fibroblasts (including papillary and reticular fibroblasts), Merkel cells, Langerhans cells, sebocytes, dermal dendritic cells, macrophages, mast cells, epithelial cells of hair follicles, fibroblasts of the hair follicle papilla, preadipocytes, stem cells (particularly stem cells of adipose cell tissue), sensitive neurons, muscle cells. These cells can be healthy or pathological.

Another subject-matter of this invention is bio-ink that can be obtained using this method. It may contain living cells, and particularly fibroblasts. Gelatin confers a viscosity on this bio-ink with a transition point (gel point) at a temperature typically between 27° C. and 32° C., and preferably between 28° C. and 30° C.: the bio-ink is fluid above this temperature and gels below this temperature. This gelling takes places particularly when the bio-ink brought to a temperature TI above its gel point drops to a temperature T2 below this gel point: in this case it can solidify immediately without spreading completely, possibly keeping the shape of the extrusion bead. Thus, the bio-ink can be used in additive deposition methods.

Another subject-matter of the invention is a method of fabricating a body tissue substitute, in which:
(i) a bio-ink according to the invention is provided;
(ii) an aqueous solution (called "polymerization solution") is provided containing between 1% and 5% by mass of calcium ions and between 2 U/mL and 40 U/mL (and preferably between 5 U/mL and 40 U/mL, and even more preferably between 10 U/mL and 30 U/mL) of thrombin;
(iii) said bio-ink is brought to a temperature T1 above its gel point and it is deposited on a substrate at a temperature T2 below the gel point of said bio-ink, at which it gels to form a controlled three-dimensional object called the "untreated printed object",
(iv) said untreated printed object is treated with said polymerization solution to consolidate said untreated printed object into a body tissue substitute;
(v) optionally, in the case in which said bio-ink contains living cells, said body substitute precursor is incubated in a cell culture medium. This incubation is advantageously done at a temperature between 36° C. and 38° C., preferably in a wet atmosphere with 5% of $CO_2$.

This process can be done by single deposition or by additive deposition, single deposition consisting of the deposition of a single layer or a single bead of ink, while additive deposition can be used to create untreated printed objects having a given controlled two-dimensional extension, or even of objects with a controlled three-dimensional shape.

In particular, this method may include deposition (single or additive) by extrusion (for example using a syringe provided with a piston or a screw), by ink jet (usually involving the projection of bio-ink droplets on a scaffold at an appropriate temperature such that the bio-ink will solidify) or by laser (for example involving the deposition of a layer of bio-ink on a layer formed from a material capable of absorbing light from the laser, the latter layer then being locally irradiated by the laser, which generates projection of ink droplets on a substrate kept at an appropriate temperature to solidify the bio-ink).

Advantageously TI is between 28° C. and 37° C. (preferably between 28° C. and 33° C.) and T2 is between 0° C. and 20° C. (and preferably between 4° C. and 18° C.).

The printed object is definitively consolidated by the treatment with the polymerization solution: although coagulation of alginate by calcium can be at least partially reversible through possible departure of calcium, coagulation of fibrinogen by thrombin is irreversible. In the process according to the invention, this consolidation is homogeneous throughout the thickness of the object.

Said untreated printed object can be treated with said polymerization solution by immersion, preferably at a temperature T3 higher than T1 and preferably between 35° C. and 38° C.

According to one particular embodiment of the invention, said body tissue precursor is a skin substitute precursor. In this case, said bio-ink is a suspension containing living fibroblast cells. Said incubation is advantageously done at a temperature between 36° C. and 38° C., in a wet atmosphere under 5% of $CO_2$. It advantageously includes a first incubation phase lasting between one and forty days, and a second incubation phase lasting between five and forty days, knowing that an aqueous suspension of keratinocytes is deposited on the surface of said skin substitute between the first and the second phase. The keratinocytes can also be deposited on the surface of said skin substitute by deposition of a bio-ink according to the invention, particularly in a thin layer.

Said skin substitute precursor may be flat or it may have another form. In one embodiment, said untreated printed object comprises an approximately flat upper surface and has a uniform distribution of fibroblasts, equal to between 0.2 and $10 \times 10^5$ (and preferably between 0.2 and $2 \times 10^5$) fibroblasts per $cm^2$ of flat upper surface.

In another embodiment, the concentration of fibroblasts is between 0.6 et $12 \times 10^5$ fibroblasts per $cm^3$ of bio-ink, preferably between 1 and $7 \times 10^5$ fibroblasts per $cm^3$ of bio-ink, and even more preferably between 1 and $5 \times 10^5$ fibroblasts par $cm^3$ of bio-ink; this is the preferred embodiment.

Still with the purpose of preparing a skin substitute, the quantity of keratinocytes deposited is advantageously between 0.05 and $50 \times 10^5$ (and preferably between 0.2 and $20 \times 10^5$ keratinocytes par $cm^2$ of flat upper surface; the most preferred concentration is between 0.5 and $10 \times 10^5$ keratinocytes per $cm^2$ of flat upper surface.

Yet another purpose of the invention is a body tissue substitute, and particularly a skin substitute (or a precursor of a skin substitute), that can be obtained by the method according to the invention.

The method according to the invention can be used to fabricate a wide variety of body substitutes. In particular it can be used to fabricate skin substitutes including a dermal layer containing particularly fibroblasts, an epidermis layer and a stratum corneum including particularly keratinocytes and melanocytes. This structure is well stratified and differentiated. The skin substitute according to the invention can be used to study the effect of cosmetic or dermatological active constituents, or for toxicological studies. It can also be used in reparative, aesthetic or plastic surgery.

For example, body substitutes made with pathological cells can be used to test the general or individual efficiency of active constituents.

DESCRIPTION OF THE FIGURES

FIGS. 1 to 17 illustrate some aspects of the invention, but do not limit the scope of the invention.

Histological and immunohistological analyses are based on techniques known to a person skilled in the art. Optical micrographs are based on tomographic sections (5 µm) encased in paraffin and fixed with formalin, colored after deparaffining and rehydration. A DS-Ri1 type CCD camera coupled to an NIS type software (Nikon company) was used to generate images in uncompressed 16-bit format (six representative observations per sample). Immunofluorescence experiments were made on 5 µm cryosections with appropriate antibodies, and the samples were observed with an Observer ZI optical microscope coupled to an LSM700 confocal laser scanning system (Zeiss) to generate images in the uncompressed 8-bit format (six representative observations per sample). Samples for transmission electron microscopy were fixed with a buffer (pH 7.5) of sodium cacodylate (0.1 M) containing 2% of glutaraldehyde at 4° C., then treated with a solution of $OsO_4$ at 1%. The samples were dehydrated then encased in an epoxy resin that had been polymerized for 3 days at 56° C. The sections were then treated with a solution of uranyl acetate (7%) and lead acetate.

Figure 1:
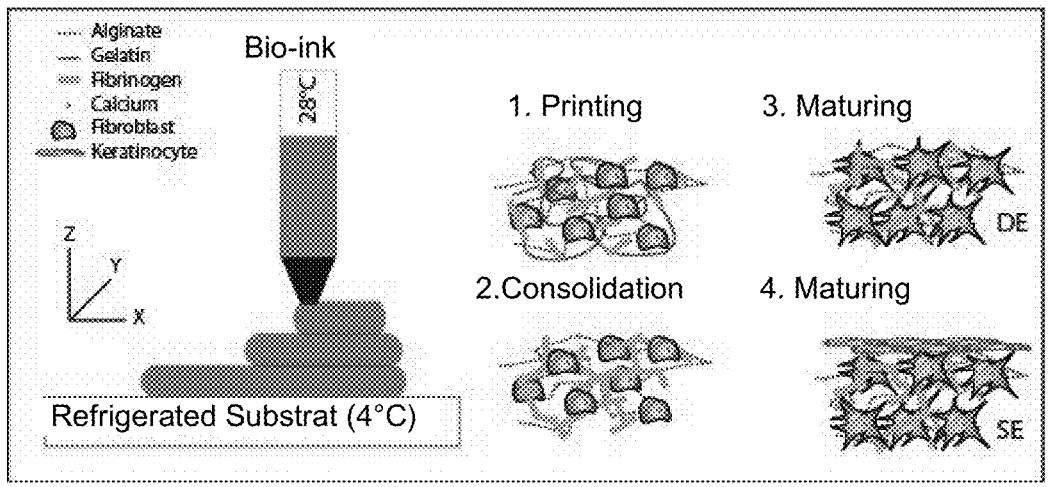

FIG. 1 diagrammatically illustrates the method according to the invention.

Figure 2:
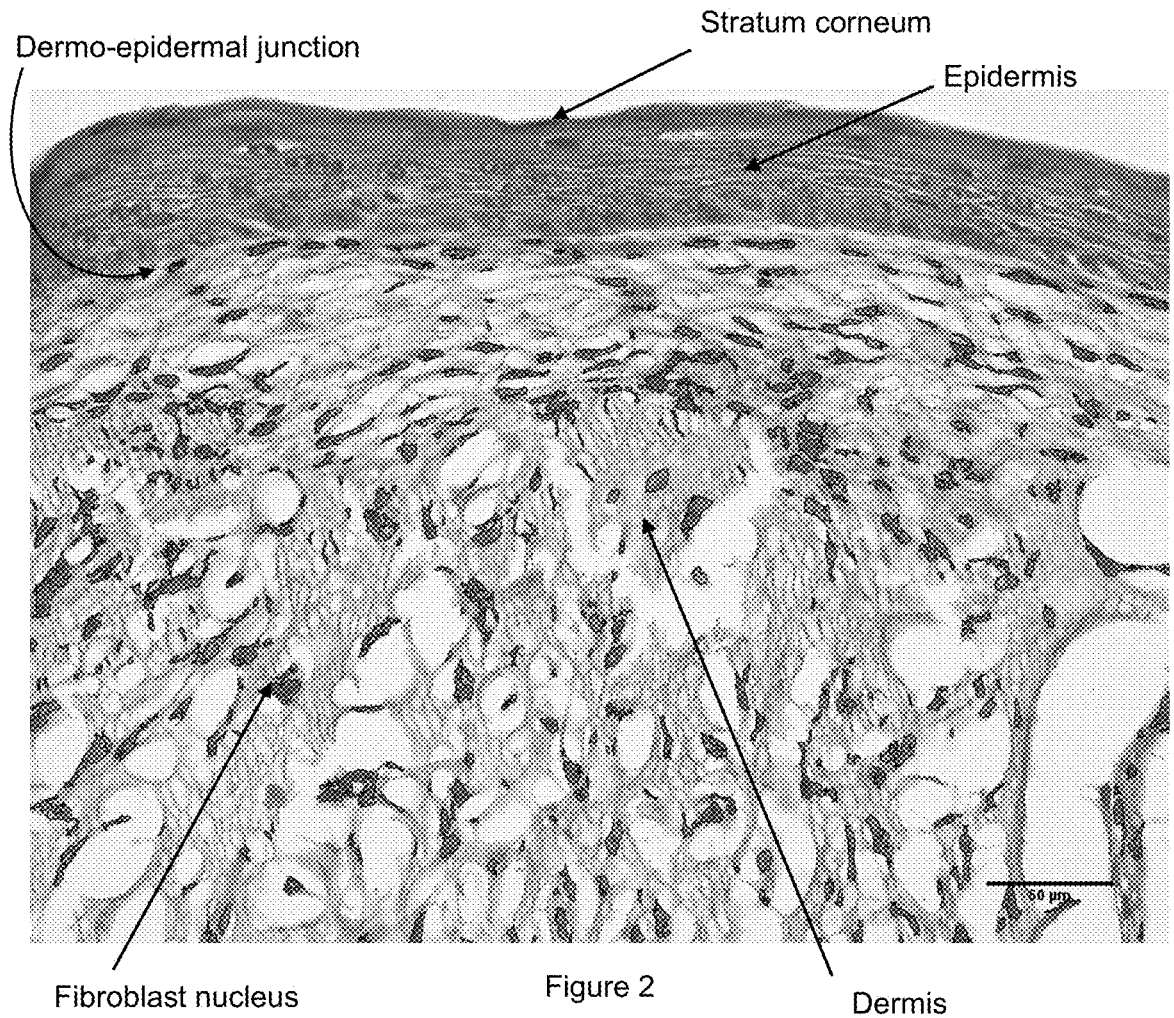

FIG. 2 relates to example 2 and shows an optical micrograph of a cross-section through a skin substitute according to the invention. The black bar at the bottom right is 50 µm long.

Figure 3:
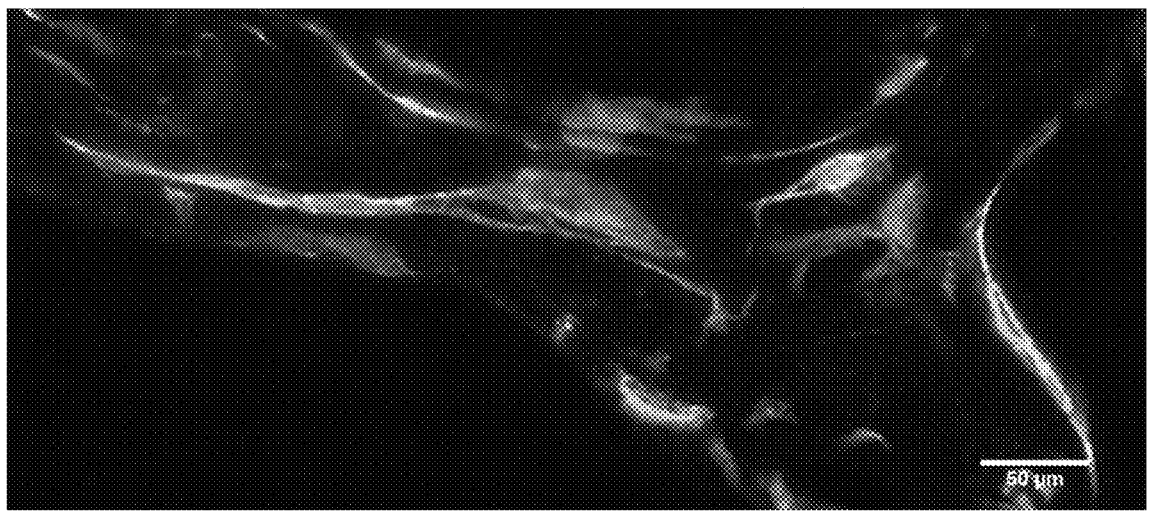

FIG. 3 relates to example 3 and shows an optical micrograph of a cross-section through a skin substitute according to the invention, with immunohistochemical marking with vimentin. The white bar at the bottom right represents a length of 50 µm.

Figure 4:
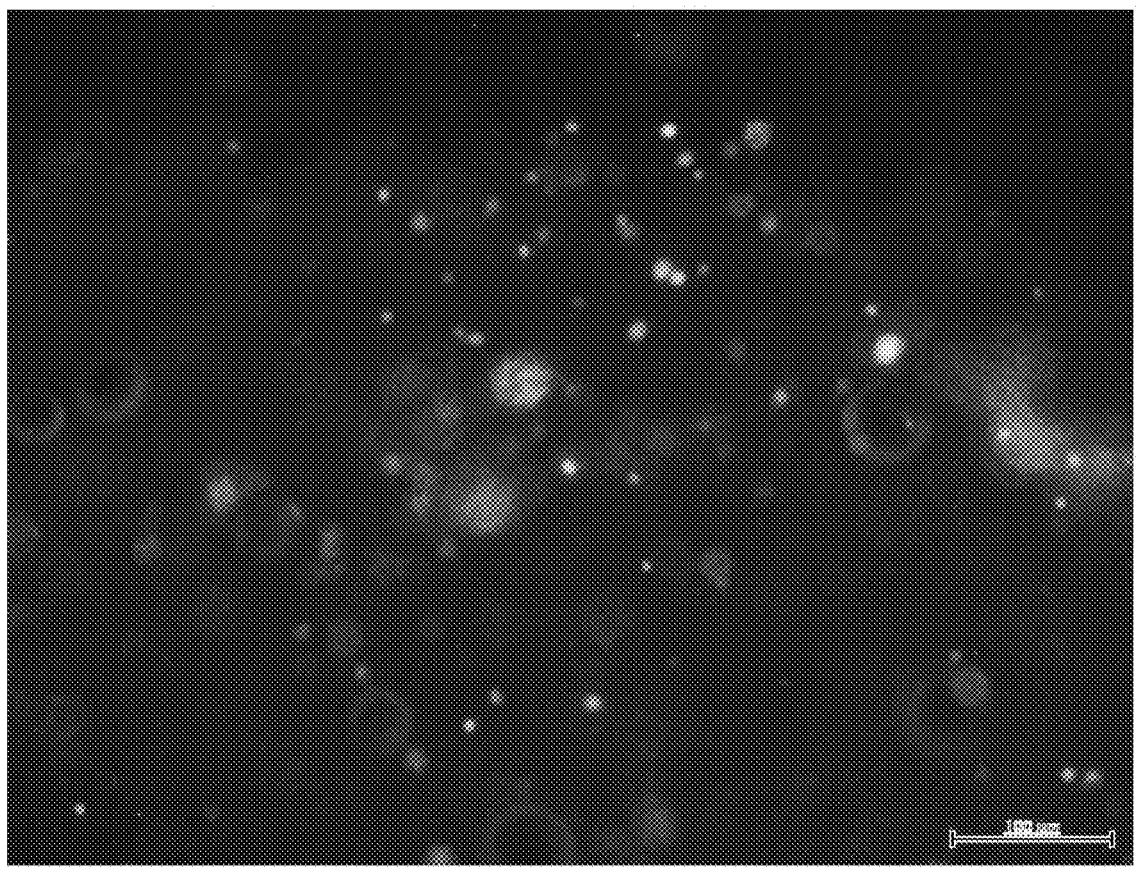

FIG. 4 relates to example 4b (not included in the invention) and shows an optical micrograph of a cross-section through a skin substitute made with bio-ink not included in the invention. The bio-ink does not contain any fibrinogen and contains NIH3T3 type fibroblasts coupled with GFP (Green Fluorescent Protein). The figure shows that when the bio-ink does not contain fibrinogen, the fibroblasts do not spread in three dimensions, do not adhere to the solidified bio-ink and eventually die.

FIG. 5 relates to example 6. FIG. 5(a) shows, for skin substitute precursors made with three inks each comprising a different concentration of living cells, the cell viability expressed as a ratio of the optical absorbance after coloring with Alamar Blue™ (measurement of the absorbance at 570 nm and 600 nm, the quantity of living cells depends on the ratio between these two absorbance values).

FIG. 5(b) shows the cell viability (determined in the same manner) after 7, 10 and 14 days of incubation for a skin substitute made using bio-ink containing 100 000 fibroblasts/mL; the increase in the number of cells reflects cell proliferation. FIGS. 5(c) and (d) show a microscopy section after staining with DAPI that generates the grey veil representing living cells, and with propidium iodide that generates white stains representing dead cells, knowing that FIG. 5(c) relates to the body substitute after 14 days of incubation, while FIG. 5(d) relates to the same body substitute after treatment with sodium dodecyl sulfate (0.5%) that kills cells (control experiment).

Figure 6A:
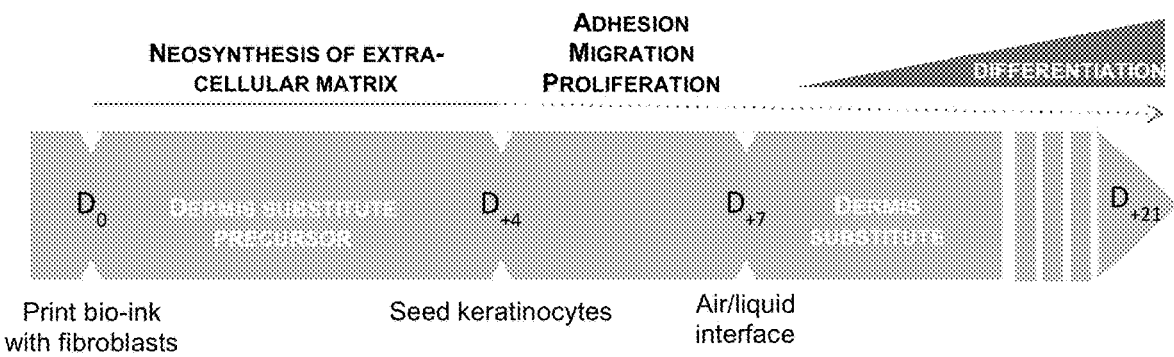
Figure 6B:
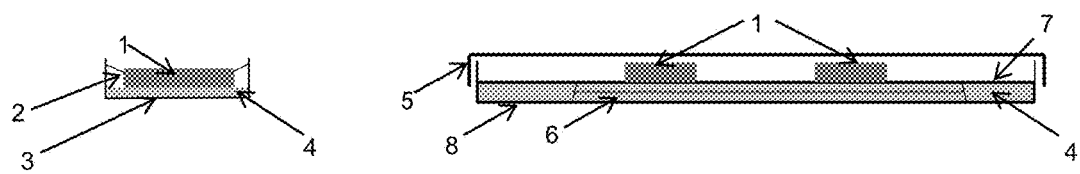
Figure 6C:
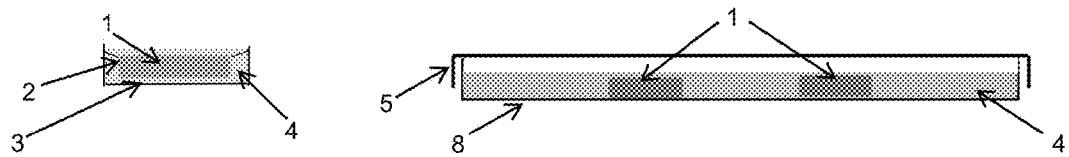

FIG. 6(a) diagrammatically illustrates the steps involved in one embodiment of the method according to the invention. FIGS. 6(b) and 6(c) diagrammatically shown the position of the sample during the first seven days of incubation immersed in the culture medium (FIG. 6(c)) and on the surface of the culture medium (FIG. 6(b)) in the well of a multi-well plate (left) and in a culture box (FIG. 6(c)).

Figure 7A:
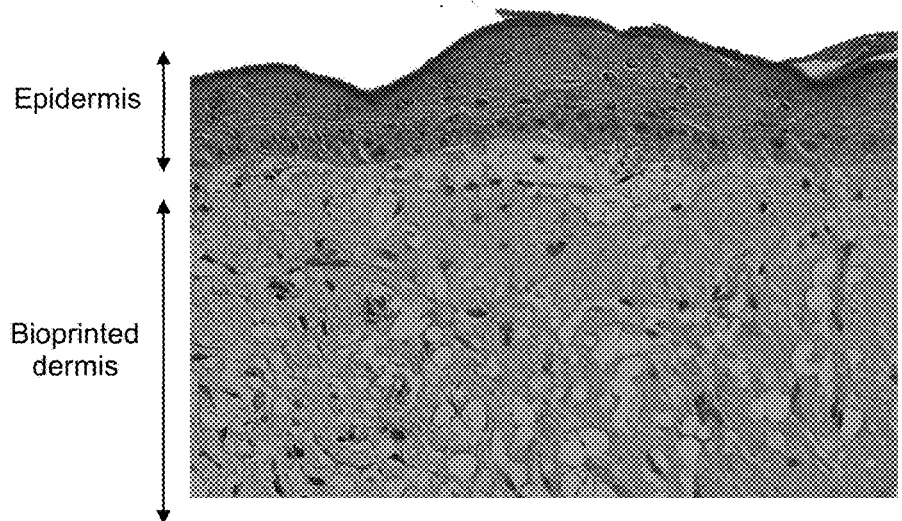
Figure 10A:
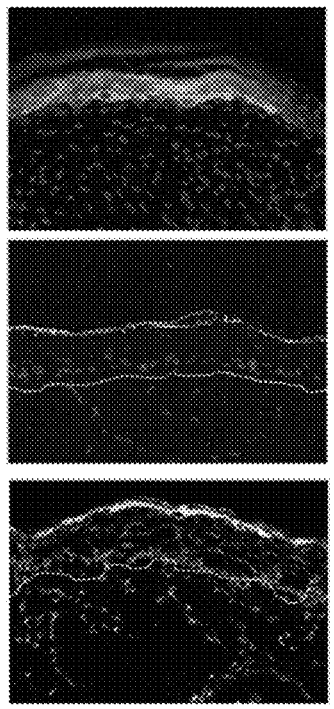

FIGS. 7(a)-7(l) to 11(a)-(e) relate to example 7 and show:
  optical microscopy sections through a skin section according to the invention (FIG. 7(a) with HPS (hematoxylin-phloxine-saffron) stain, FIG. 7(b) with Masson's trichrome stain);
  Specific immuno-histological images (FIGS. 7(c), (d), (e),(f)*,(g)*,(h)*,(i),(j),(k)* and (l)*, FIGS. 10(a),(b), (c),(d)*,(e)*,(f)*, as explained in the example, knowing that figures marked with an asterisk relate to healthy human skin, and the others relate to the dermal substitute according to the invention;
  Transmission electron microscopy images (FIGS. 8(a), (b),c),(d), FIGS. 11(a),(b),(c),(d),(e)) for a dermal substitute according to the invention.

FIGS. 12, 13, 14 and 15 relate to examples 8, 9, 10 and 11 respectively and show cell proliferation curves after incubation of body substitutes according to the invention.

FIGS. 16(a)-16(d) relates to example 12 and shows cell viability curves for two different bio-inks according to the invention (FIGS. 16(a),(b)), each prepared in 4 different concentrations, and micrographs (FIGS. 16(c) and (d)). One is prepared with adipose tissue stem cells (FIG. 16(a)) and the other with preadipocytes (FIG. 16(b)), two types of adipocyte precursors. When these hypodermis substitutes are bio-printed with the method according to the invention and then differentiated with differentiation factors (known to a person skilled in the art), a functional hypodermis is obtained because the cells have lipidic vacuoles full of fatty acids typical of adipocytes. The micrograph in FIG. 16(c) shows immuno-marking with perilipin A, a protein typically expressed on the surface of lipidic droplets. The micrograph in FIG. 16(d) shows a coloring of the lipidic content of cells, this coloring having being obtained with Nile red, a stain specific to lipids.

Figure 17A:
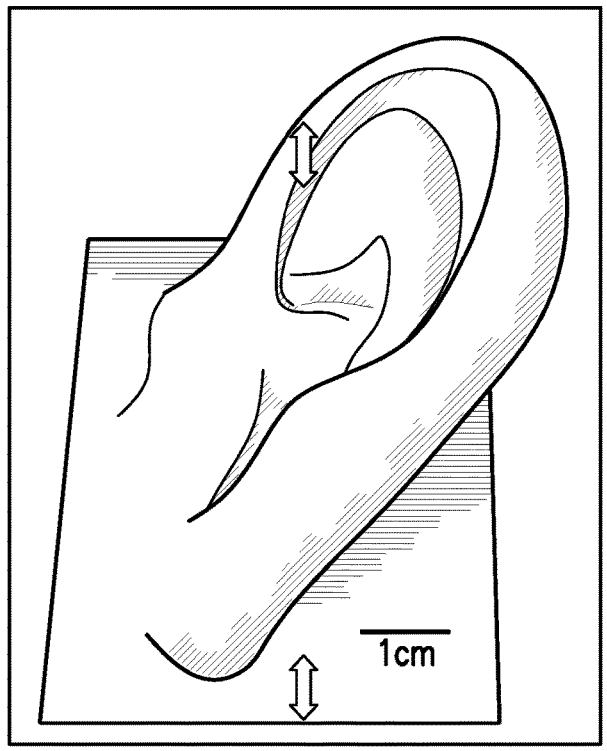
Figure 17B:
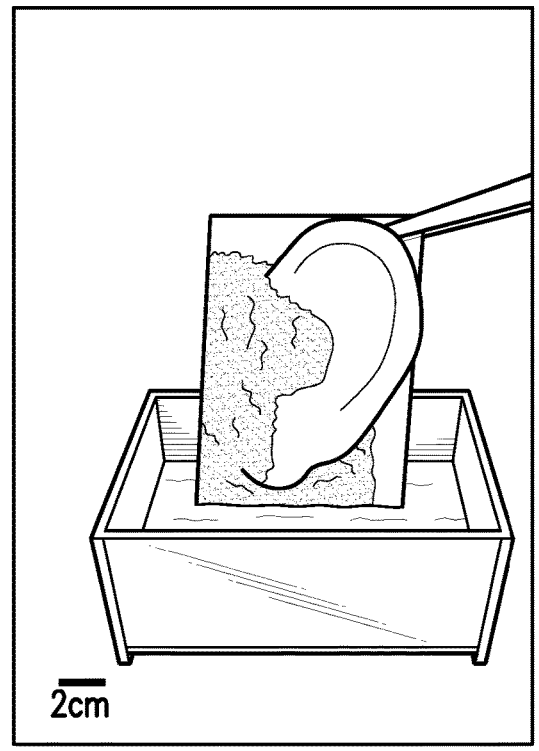
Figure 17C:
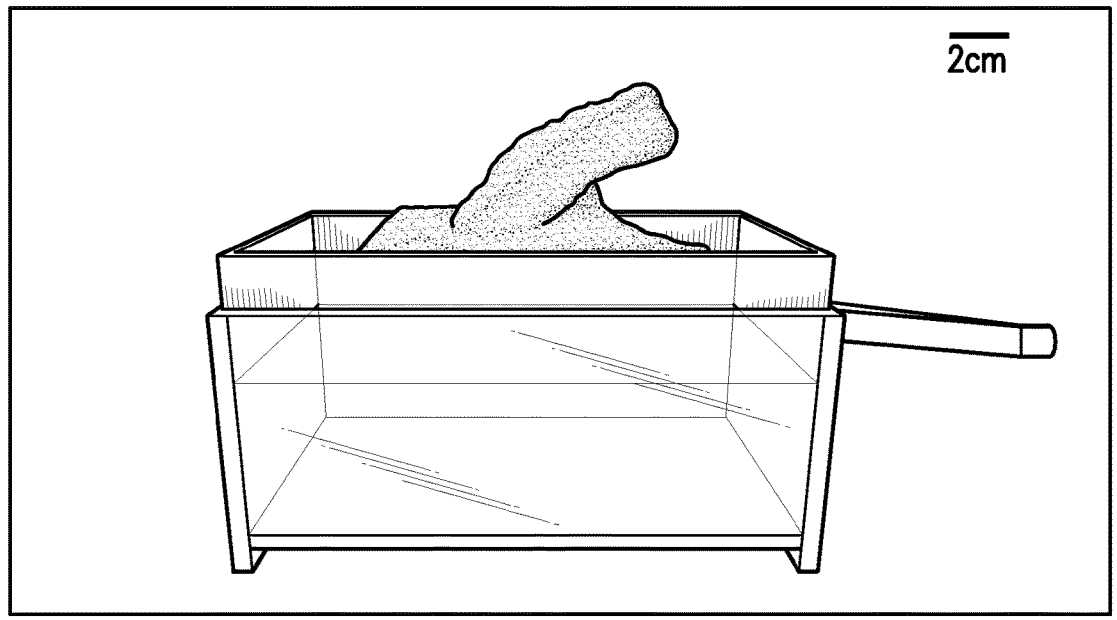

FIGS. 17(a)-17(c) relates to example 13, showing illustrations of a body substitute precursor made according to the invention at different stages of fabrication.

DETAILED DESCRIPTION

The invention can be used to create body substitutes, and particular equivalent dermises, by means of additive deposition (such as 3D printing). This new fabrication method saves time and offers an extremely advantageous, simple and reproducible way to fabricate body substitutes (and particularly dermal substitutes). Fabrication and maturing times are very much shortened. In particular, this fabrication method can use the following additive deposition techniques: deposition (single or additive) by extrusion, ink jet deposition and laser deposition.

Bio-ink according to the invention is composed of a mix of biomaterials that can form a hydrogel and cells. It can also be prepared just before use from stable aqueous solutions. Once solutions have been prepared in the right concentrations, they simply need to be mixed carefully with a suspension of cells (if the objective is a skin substitute: typically fibroblasts) in an extrusion syringe. The syringe is then mounted on the bio-printer. Advantageously, a syringe pusher is provided to have control over the flow; for example, the syringe pusher can be controlled by a worm screw and a motor that applies constant pressure on the liquid or gel to be extruded. Thus, a hydrogel object is printed; this object is typically a flat object. Once the hydrogel has been printed, it has to be immersed in a biocompatible polymerization solution that will make it possible for the biomaterials to form a solid network and to maintain the required three-dimensional shape. The cells are then left to develop in a step also called the "maturing step". During this cell development into a three-dimensional network, the printed cells (fibroblasts in the case of a skin substitute) contained in the polymerized hydrogel secrete their extracellular matrix. The hydrogel will then be progressively resorbed to leave space for the emergence of a neosynthesized tissue in which specific functions will appear, which is a definite advantage compared with a "scaffold" type approach in which the biomaterials are sometimes non-resorbable.

If the objective is a skin substitute, keratinocytes are advantageously added by deposition of a bio-ink according to the invention or by seeding the surface; this step is followed by an appropriate incubation and can thus result in a stratified and differentiated skin substitute comprising the dermis, the dermo-epidermal junction, the epidermis and the stratum corneum.

For implementation of the method according to the invention, the bio-ink must be prepared according to a precise and predefined order and proportions.

In a first step, alginate and gelatin powders are provided, they are sterilized and solubilized to obtain two stock solutions: the first is an aqueous solution of gelatin, obtained by dissolution of gelatin powder (preferably at a concentration of between 5% m/v and 40% m/v) in a solution of NaCl (preferably at a concentration of between 0.2% m/v and 5% m/v, more preferably between 0.4% m/v and 3% m/v, and most preferably between 0.5% m/v and 1.4% m/v), the second is an aqueous solution of alginate, obtained by dissolution of alginate powder (preferably "Very Low Viscosity" quality) at a concentration of between 1% m/v and 10% m/v (preferably between 2% m/v and 7% m/v) in a solution of NaCl (preferably at a concentration of between 0.2% m/v and 5% m/v, more preferably between 0.4% m/v and 3% m/v, and most preferably between 0.5% m/v and 1.4% m/v). These two solutions are stable and can be stored.

Advantageously, the same NaCl solution is used to prepare these two solutions. The following ranges of concentration are particularly advantageous:

Gelatin solution between 6% m/v and 30% m/v, alginate solution between 1% m/v and 8% m/v; NaCl solution between 0.2% m/v and 3% m/v (preferably between 0.4% m/v and 2% m/v, and more preferably between 0.5% m/v and 1.4% m/v).

Gelatin solution between 10% m/v and 30% m/v, alginate solution between 2% m/v and 6% m/v; NaCl solution between 0.2% m/v and 3% m/v (preferably between 0.4% m/v and 2% m/v, and more preferably between 0.5% m/v and 1.4% m/v).

Gelatin solution between 15% m/v and 26% m/v, alginate solution between 2% m/v and 6% m/v (and preferably between 3% m/v and 5% m/v); NaCl solution between 0.2% m/v and 3% m/v (preferably between 0.4% m/v and 2% m/v, and more preferably between 0.5% m/v and 1.4% m/v).

Gelatin solution between 17% m/v and 24% m/v, alginate solution between 2% m/v and 6% m/v (and preferably between 3% m/v and 5% m/v); NaCl solution between 0.4% m/v and 2% m/v (preferably between 0.5% m/v and 1.4% m/v, and more preferably between 0.6% m/v and 1.3% m/v).

The role of NaCl in these solutions is to favor an osmotic environment favorable to cell development in the bio-ink, and to facilitate dissolution of the alginate.

The alginate powder is a commercially available powder, and the "Low Viscosity" quality is preferred, the "Very Low Viscosity" quality being even more preferred.

If the bio-ink contains too much alginate, it will become too hard for use with additive deposition techniques, and if it does not contain enough, it will be insufficiently polymerized by calcium ions and the resulting precursor may not be sufficiently solid.

If the bio-ink contains too much fibrinogen, it will become too hard for use with additive deposition techniques, and if it does not contain enough, the cells will not adhere to the bio-ink, they will not spread and will finally perish. This is the reason why a concentration by mass of 0.2% of fibrinogen is necessary in the bio-ink, and preferably the minimum content is 0.3%. Similarly, the thrombin concentration must be chosen such that fibrinogen can be transformed into fibrin.

Furthermore, a third solution is prepared that is an aqueous solution of fibrinogen, preferably at a concentration between 1% m/v and 15% m/v (more preferably between 3% m/v and 12% m/v, and even more preferably between 5% m/v and 10% m/v) in which an appropriate cell concentration was added (typically between 0.05 and 1 million cells/mL (preferably between 0.1 and 0.6 million per mL). For example, for a deposition test of a skin substitute precursor, we could prepare 2 mL of this solution. Said cells are particularly fibroblasts.

The cell concentration in the bio-ink is critical for success of the method for preparing the body substitute according to the invention. If it is too low, the cells are incapable of forming a tissue sufficiently similar to the target native tissue. For example, in the case of fibroblasts, the extracellular matrix formed is insufficient to replace the constituents of the bio-ink. In the case of epithelial cells such as keratinocytes, it is observed that the cells are not contiguous and finally die.

If the cell concentration in the bio-ink is too high, the structure degrades instead of developing, and surprisingly it is observed that its texture changes and it becomes unusable (it literally "melts").

In a third step, the bio-ink is prepared from these three solutions to obtain a mix that contains about 35% to 65% (preferably about 45% to 55%, and even more preferably about 50%) of the first solution (gelatin), about 15% to 35% (preferably between 20% to 30%, and even more preferably about 25%) of the second solution (alginate) and about 15% to 35% (preferably about 20% to 30%, and even more preferably about 25%) of the third solution for a total of 100%, these percentages being expressed as a percent by volume.

In a fourth step, a fourth aqueous solution is prepared that is the polymerization solution. It contains calcium in solution at about 1 to 5% m/v and preferably about 3% m/v, to which thrombin is added at a final concentration of about 10 U/mL. This polymerization solution must be procured in a sufficient quantity so that the object obtained by 3D printing can be immersed so as to obtain a homogeneous polymerized gel. This fourth step can be performed before or after or during the previous three steps, but the storage time of this fourth solution is limited; the inventors have observed that solidification and polymerization of the bio-ink are more homogeneous when the fourth solution is prepared just before use.

If said fourth solution does not contain enough calcium, polymerization of the alginate does not occur or is not sufficient. If it contains too much calcium, the viability of cells will be reduced since calcium can be cytotoxic.

Printing is done in a fifth step, in other words ink is deposited on a scaffold. Before doing this, the temperature T1 of the ink is increased sufficiently to melt the gelatin. This temperature TI depends on the exact composition of the ink and must be determined by simple tests: for the most preferred composition range mentioned above, a temperature T1 of the order of 28° C. to 29° can be suitable. This printing can be done by any appropriate means, for example using a syringe mounted on a carriage, on which the syringe is displaced along an axis and the carriage is displaced in a direction orthogonal to said axis. The substrate is placed on a table or platform. A displacement along the height axis can be provided, either for the carriage carrying the syringe, or for the substrate carrier table or platform.

The substrate is advantageously cooled so that the gelatin solidifies immediately; this substrate temperature T2 depends on the composition and temperature T1 of the ink and the rate of its deposit; it can be determined by simple tests. In another embodiment, the print assembly is located in a cold room, in other words at temperature T2, optionally the syringe can be heated to temperature T1. This embodiment is advantageous in that that thicker or more complex shaped structures can be fabricated, for which heat conduction through the ink layer that has just been deposited makes it impossible for the ink layer currently being deposited to be cooled quickly enough.

In a sixth step, the untreated printed object is consolidated by treating it with the polymerization solution (fourth solution), preferably by total immersion; the result obtained is thus a so-called "solidified object". The contact time between the untreated printed object and the polymerization solution is preferably at least fifteen minutes. During this step, the temperature T3 of the polymerization solution is preferably higher than the melting temperature of gelatin. This means that the gelatin can change to the aqueous phase, and thus the largest part of the gelatin is removed from the solidified object. The result obtained is thus called a "body tissue precursor", that can be a "skin tissue precursor". The temperature T3 may be about 37° C.

Steps 5 and 6 are diagrammatically illustrated on FIG. 1.

In a sixth step, the body tissue precursor (that can be a skin substitute precursor) is incubated to obtain a substitute body tissue (for example a skin substitute). This incubation is done in three phases. During a first incubation phase, said skin substitute precursor is immersed in an appropriate fibroblast culture medium, preferably at a temperature of about 37° C. The duration of this incubation can be between three and twenty days (up to 40 days with keratinocytes); a duration of between eight and fifteen days is preferred; a duration of twelve days is optimal for fibroblasts.

At the end of this first incubation phase, an aqueous suspension of keratinocytes is applied on the surface of the skin substitute precursor. A concentration of between 1 and $5 \times 10^5$ cells par cm² is suitable.

Then, during a second incubation phase, the skin substitute precursor is immersed in an appropriate culture solution, for example Green's medium; nutrients have to be added regularly (preferably every day). This second incubation phase lasts between five and ten days, preferably about seven days. The temperature is 37° C.

And finally, during a third incubation phase, the skin substitute precursors are kept on the surface of the differentiation culture medium and they are incubated for between 15 and 30 days, preferably between 18 and 25 days, typically 21 days. The temperature is 37° C. Thus, a skin substitute is obtained. Said differentiation medium typically comprises DMEM and specific additives; in one advantageous embodiment these additives are hydrocortisone (0.4 μg/mL), insulin (5 μg/mL), bovine albumin (8 mg/mL).

The bioprinting process according to the invention can be used to obtain objects with dimensions of a few centimeters or even decimeters. The printer resembles a classical FDM (Fused Deposition Modelling) 3D printer, but the syringe pusher then replaces the plastic extruders.

The bio-ink according to the invention satisfies three objectives:
Keep an adequate rheology for the hydrogel during the printing (extrusion) process,
Formation of a homogeneously polymerized object that will keep its 3D shape obtained,
Enable the development of a cell lattice in 3D.

These three functions have been validated by the use of the following biomaterials. Gelatin, a collagen-based polymer with a phase transition temperature of 29° C., was used as a rheological component, that assures that the bio-ink remains on a cooled substrate after printing, and can subsequently be eliminated in later steps of the method. Alginate, a carbon hydrate polymer with the property of forming a hydrogel in the presence of calcium, used as a structural element, confers mechanical stability on the printed bio-ink once the gelatin has been solubilized. Fibrinogen, a glycoprotein with the ability to form a hydrogel under the action of thrombin, used both as a construction and maturing element due to its cellular bonding components (RGD patterns).

FIG. 6(a) diagrammatically illustrates the procedure of the method used. The method according to the invention includes deposition of a skin substitute precursor containing normal human dermal fibroblasts (NHDF). Incubation takes place under total immersion for four days in a culture medium at 37° C. to stimulate synthesis of the extracellular matrix. The next step is to seed normal human epidermal keratinocytes (NHEK) and leave to incubate for another three days to stimulate cell proliferation, migration and adhesion. After the seventh day after the beginning of incubation, incubation is continued at the air-liquid interface to obtain cell differentiation until a total of 21 days.

Incubation can be done in the well of a multi-plate well or in a Petri box. FIG. 6(c) diagrammatically shows incubation conditions under immersion (used for the first seven days); at the left in the multi-well plate 3, and at the right in a culture box. In the "multi-well plate" variant, the bio-printed body substitute precursor 1 is placed in a culture insert 2 located in the well 3 of a multi-well plate. The culture medium 4 covers the body substitute precursor 1. In the "culture box" variant, the bio-printed body substitute precursor 1 is placed in a tank 8 containing the culture medium 4; a lid 5 covers the tank 8.

FIG. 6(b) diagrammatically shows incubation conditions in emersion (used starting from the eighth day); at the left in the multi-well plate 3, and at the right in a culture box. In the "multi-well plate" variant, the body substitute 1 is placed in a culture insert 2, the lower surface of which touches the upper surface of the culture medium 4 located in the well 3 of a multi-well plate. In the "culture box" variant, the body substitute 1 is placed on a stainless steel grating 6 that is slightly immersed in the culture medium 4 contained in a tank 8. The upper surface of the grating 6 is covered with a sheet of blotting paper; a lid 5 covers the tank 8.

The invention has many applications. The method of fabricating a body tissue substitute according to the invention can be used to fabricate different natures of body tissue substitutes. All types of living cells can be incorporated into the bio-ink according to the invention. For example all other types of skin cell can be incorporated into the bio-ink (particularly ADSC (Adipose-Derived Stem Cells), adipocytes and preadipocytes, endothelial cells, nerve cells, dermal dendritic cells, Langerhans cells, melanocytes, Merkel cells, sebocytes, macrophages; mast cells, hair follicle epithelial cells, fibroblasts of the hair follicle papilla, induced pluripotent stem cells. In particular, the method can be used to fabricate substitutes for a variety of body tissues, and particularly substitutes for the cornea, the oral mucosa, the esophagus, cartilage, vessels, vaginal mucosa.

In general, all types of cells, preferably living cells, can be incorporated in the framework of this invention.

Cells may be embryo stem cells (totipotent, pluripotent and tripotent) or differentiated (germ-line cells or somatic cells), primary cells isolated from all human or animal tissue or organ, for example germ-line cells (gametes), somatic cells and adult stem cells. Cells can originate particularly from connective tissue or support tissue (such as bone, ligament, cartilage, tendon, adipose tissue), muscle tissue (such as smooth muscle cells of the vascular wall, cardiac muscle, skeletal muscle), nerve tissue and epithelia (such as blood vessels, Wharton's duct, oral mucosa, dorsum of the tongue, hard palate, esophagus, pancreas, adrenal gland, prostate, liver, thyroid, stomach, intestine, small intestine, rectum, anus, gall bladder, thyroid follicle, lymphatic vessel, skin, sweat gland, mesothelium of body cavities, ovary, uterine tube, uterus, endometrium, cervix (endocervix, exocervix), vagina, labia majora, tubuli recti, rete testis, efferent ducts, epididymis, vas deferens, ejaculatory duct, bulbourethral gland, seminal vesicle, oropharynx, larynx, vocal cord, trachea, bronchioles, cornea, nose, proximal convoluted tubule of the kidney, distal tube of the kidney, renal pelvis, ureter, urinary bladder, prostatic urethra).

Cells may be cells of mesodermal, ectodermal or endodermal origin.

Human or animal cells may be selected from the group composed of lymphocytes (particularly B lymphocyte, T lymphocyte, cytotoxic T lymphocyte, NKT lymphocyte, regulatory T lymphocyte, auxiliary lymphocyte), myeloid cells, granulocytes, basophil granulocytes, eosinophil granulocytes, neutrophil granulocytes, hyper segmented neutrophils, monocytes, macrophages, reticulocytes, trombocyte, mast cells, thrombocytes, megakaryocytes, dendritic cells, thyroid cells, thyroid epithelial cells, parafollicular cells, parathyroid cells, parathyroid chief cells, oxyphil cells, adrenal cells, chromaffin cells, pineal cells, glial cells, glioblasts, astrocytes, oligodendrocytes, microglial cells, magnocellular neurosecretion cells, stellar cells, Boettcher cells; pituitary cells, gonadotrophs, corticotrophs, thyrotrophs, somatotroph, lactotrophs, lung cells (type I pneumocytes, type II pneumocytes, Clara cells); goblet cells, alveolar macrophages, myocardiocytes, pericytes, gastric cells (gastric chief cells, parietal cells, goblet cells, Paneth cells, G cells, D cells, ECL cells, I cells, K cells, S cells, enteroendocrine cells, enterochromaffin cells, APUD cells), liver cells (hepatocytes, Kupffer cells), bone cells (osteoblasts, osteocytes, osteoclasts, odontoblasts, cementoblasts, ameloblasts), cartilage cells (chondroblasts, chondrocytes), hair cells (trichocytes), skin cells (keratinocytes, adipocytes, fibroblasts, melanocytes, nevus cells), muscle cells (myocytes, myoblasts, myotubes), tendon cells, kidney cells (podocytes, juxtaglomerular cells, intraglomerular mesangial cells, extraglomerular mesangial cells, macula densa cells), sperms, sertoli cells, Leydig cells, ovocytes.

Cells can also be isolated from a diseased tissue, for example a cancer tissue.

For example, cells can be isolated or derived from many types of cancer: breast cancer; biliary tract cancer; bladder cancer; brain cancer including glioblastomas and medulloblastomas; cervical cancer; choriocarcinoma; colon cancer; endometrial cancer; esophageal cancer; stomach cancer; hematological neoplasia including leukemias; intraepithelial neoplasia including Bowen's disease and Paget's disease; liver cancer; lung cancer; lymphoma including Hodgkin's disease; neuroblastomas; oral cancers including epidermoid carcinoma; ovary cancer including cancers of epithelial cells, stromal cells, germ-line and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cells carcinoma, Kaposi's sarcoma, basal cell carcinoma, and epidermoid carcinoma; testicular cancer including germ-line cell tumors such as seminoma, non-seminomas (teratomas, choriocarcinomas), stromal tumors, and germ-line cell tumors; thyroid cancer including thyroid adenocarcinoma and medullary carcinoma; kidney cancer including adenocarcinoma and Wilms' tumor.

Cells may be umbilical cord blood cells, stem cells, embryo stem cells, adult stem cells, cancer stem cells, progenitor cells, autologous cells, isograft cells, allogenic cells, xenograft cells and genetically modified cells. The cells may be induced progenitor cells. Cells may be cells isolated from a subject, for example a donor subject, who has been transfected with a gene associated with stem cells to induce pluripotence in the cells. Genes associated with stem cells may be chosen from the group composed of Oct3, Oct4, Sox1, Sox2, Sox3, Sox15, Klf1, Klf2, Klf4, Klf5, Nanog, Lin28, C-Myc, L-Myc and N-Myc. The cells can be cells that have been isolated from a subject transfected with a gene associated with stem cells to induce pluripotence and differentiated along a predetermined cell line.

Thus, the body tissue substitute according to the invention can be used not only as a skin substitute for tests on cosmetic, pharmaceutic and chemical products, but also for clinical applications, for example in reparative and reconstructive surgery. For example, the skin substitute according to the invention can be used as skin for burn victims. The method of fabrication of a body tissue substitute by additive deposition according to the invention can also be used to fabricate complex objects and thus to fabricate ear or nose substitutes, for example, using cells taken from the patient for which said body substitute is intended.

In general, body substitutes according to the invention can be implanted in the body of a patient (human or animal), can be used as a model to study substances of interest (particularly pharmacological or cosmetic, or to characterize chemical substances), or can be used as a model object for teaching (particularly for practical work and for surgery preparation tests). Advantageously, body substitutes according to the invention can be used for the following surgical applications: skin and cartilage (ears, nose) for victims of severe burns, implantation of gums, artificial esophagus, artificial urethra and ureter, cornea.

Furthermore, the body skin substitute according to the invention can be used to characterize the toxicity, efficiency or penetration of various chemicals in the body tissue. It can also be used for allergen tests.

Obviously, this invention can be applied indifferently to human cells and to other animal cells, particularly other mammal cells.

EXAMPLES

The following examples illustrate some aspects of the invention, but do not limit its scope.

Example 1: Culture and Collection of Cells

This example illustrates a method for amplification and collection of cells (fibroblasts and keratinocytes) that can then be used in the fabrication of the skin substitute according to the invention.

Dermal keratinocytes and fibroblasts were isolated from a human preputium.

The keratinocytes were cultivated on human fibroblasts irradiated using a technique well known to a person skilled in the art, using the culture medium known as "Green's medium" containing DMEM and Ham's F12 (in the ratio 3:1), to which adenine was added (24.3 µg/mL) with the human epidermal growth factor (10 ng/mL), hydrocortisone (0.4 µg/mL), insulin (Humulin®, 5 µg/mL), $2\times10^{-9}$ M tri-iodo-L-thyronine (5 µg/mL), $10^{-10}$ M isoproterenol, penicillin (100 U/mL), streptomycin (100 µg/mL) and 10% of fetal bovine serum. The keratinocytes collected during passes 2, 3 and 4 were used.

The fibroblasts were cultivated in an appropriate medium containing DMEM, 20% of new-born calf serum and antibiotics, at 37° C. in an atmosphere containing 5% $CO_2$. The fibroblasts collected during passes 5, 6, 7 and 8 were used.

Example 2: Deposition by Additive Technique (Method According to the Invention)

A first aqueous solution of gelatin was prepared by dissolving a gelatin powder at 20% m/v in a solution of NaCl at 0.9% m/v. A second aqueous solution of alginate was prepared by dissolving alginate powder (Very Low Viscosity) at 4% m/v in a solution of NaCl at 0.9% m/v. A third aqueous solution of fibrinogen was prepared at 8% m/v into which fibroblasts were added in suspension (obtained in example 1) at a cell concentration of 2 million cells/mL.

These three solutions were then mixed so as to obtain a mixture (called "bio-ink") that contains 50 vol-% of the first solution (gelatin), 25 vol-% of the second solution (alginate) and 25 vol-% of the third solution (fibroblasts recovered in fibrinogen).

An aqueous polymerization solution was prepared containing 3% m/v calcium and thrombin at a final concentration of 20 U/mL.

Said bio-ink has a viscous transition at 29° C. It was heated to a temperature of about 30° C. and used at this temperature for additive deposition according to a known type of deposition technique, through a syringe fitted with a syringe pusher so that the flow could be controlled. The substrate was at a temperature of about 4° C., and consequently the deposited ink solidified immediately. Starting from a 300 µm diameter bead, several layers were deposited with a total thickness of about 10 mm over an area of the order of several square centimeters. The result obtained was thus flat objects with a uniform distribution of fibroblasts, at a density of $2.5\times10^5$ fibroblasts per $cm^2$.

Each untreated printed object deposited in this way was then dipped into the polymerization solution to cross-link and coagulate the fibrinogen held at a temperature of 37° C. to polymerize the alginate and coagulate the fibrinogen. The flat object thus obtained in this case is called the "skin substitute precursor".

Example 3: Maturing of the Skin Substitute Precursor (Method According to the Invention)

Skin substitute precursors were incubated for 12 days in a fibroblast culture medium containing 1 mM of ascorbic acid 2-phosphate; they were nourished every day. After twelve days, keratinocytes were applied on the surface of skin substitute precursors with a concentration of $2.5\times10^5$ cells per $cm^2$.

Skin substitute precursors were incubated for a first seven-day incubation period immersed in Green's medium as described above, with a concentration of 1 mM of ascorbic acid 2-phosphate and antibiotics; they were nourished every day.

The skin substitute precursors were then incubated during a second 21-day incubation period, kept at the surface of the liquid in a differentiation medium containing DMEM with hydrocortisone (0.4 µg/mL), insulin (5 µg/mL), ascorbic acid 2-phosphate and antibiotics; the differentiation medium contained 8 mg/mL of bovine serum albumin.

Skin substitutes were thus obtained. They can be used to perform tests of cosmetic or chemical products.

FIG. 2 shows a cross-section through such a skin substitute. The epidermis can be seen comprising a genuine stratum corneum at its periphery, and comprising keratinocytes. The dermo-epidermal junction is sharply defined. The dermis comprises fibroblasts (only the nuclei can be seen on FIG. 2, surrounded by a black line). Pores can be seen in the dermis; these pores progressively fill the extracellular matrix secreted by the fibroblasts.

FIG. 3 shows intermediate filaments of the fibroblasts cytoskeleton in the dermis substitute (immuno-histochemical marking with vimentin). The three-dimensional form of the cytoskeleton can be seen, that resembles that found in a healthy natural dermis.

Example 4: Various Tests that were not Satisfactory

This example includes attempts to fabricate dermis substitutes using methods according to the state of the art or new methods that were not satisfactory.

Example 4a: Photopolymerizable Ink Based on PEG Diacrylate

A skin substitute precursor was prepared using a bio-ink based on photopolymerizable PEG-DA (polyethylene glycol diacrylate) using a method similar to that described with reference to this invention. The photoinitiator was Irgacure™ 819 (Bis(2,4,6-trimethylbenzoyl)-phenylphosphine oxide, by CIBA). After incubation, a cell mortality ratio of 100% was observed after 2 days. Without wishing to be bound by this theory, the inventors believe that it is not the photoinitiator as such that is cytotoxic, but the free radicals the generation of which is promoted by the photoinitiator.

Example 4b: Ink According to the Invention but without Fibrinogen

A bio-ink without fibrinogen was produced, that was conforming with the invention for all the other ingredients, with fluorescent mouse fibroblasts in the NIH3T3 line. A skin substitute precursor was prepared from this bio-ink using the steps in the method according to the invention. In this case, despite good retention of the gel, the cells did not develop satisfactorily during incubation due to lack of a cell adhesion pattern within the gel. As can be seen on FIG. 4, the cells do not spread and finally perish. Therefore this skin substitute cannot be used for tests of cosmetic, pharmaceutical and chemical products.

Example 4c: Ink Too Fluid

The method according to the invention was used, using different types of alginates that were distinguished particularly by their viscosity: "Low Viscosity" and "High Viscosity" instead of "Very Low Viscosity". It is seen that a satisfactory extrusion is not obtained with "High Viscosity" ink. The method can be adjusted to obtain untreated printed objects with "Low Viscosity" ink, but this embodiment makes the extrusion less stable, and is not preferred.

Example 4d: Other Causes of Failure

Failures (formation of a skin substitute precursor with poor morphology and/or quality) were observed in the following cases:
Contact time between the bio-ink after application and the polymerization solution too short (less than about fifteen minutes);
Total immersion fault of the bio-ink deposit during its polymerization;
Ageing of the polymerization solution.

Example 5: Fabrication of Total Skin with the 3 Skin Layers (Hypodermis, Dermis and Epidermis (Method According to the Invention)

The three skin layers can be printed using the same method but with three different syringes containing the bio-ink and the different cells:
A first syringe contains pre-adipocytes and/or mature adipocytes diluted in the bio-ink. This hypodermis is printed in several layers. It is printed first to form the deepest layer of the skin.
The second syringe contains fibroblasts in the bio-ink as described in the method. This part of the dermis is printed in several layers on the surface of the previously printed hypodermis.
The third syringe contains keratinocytes diluted in a slightly different bio-ink. This epidermis is printed in one or in several layers on the surface of the dermis layer. Melanocytes in a proportion from 1/10 to 1/2 can be added to the keratinocytes suspension at any time, to obtain pigmented skins.

Example 6: Bio-Inks According to the Invention, with Variable Content of Cells

Three bio-inks according to the invention were prepared, the only difference between them being their content of living cells (human fibroblasts): 50,000 cells per mL of bio-ink, 100,000 cells per mL of bio-ink and 200,000 cells per mL of bio-ink. Dermal substitute precursors were made with these bio-inks using the method according to the invention. The printed dermal substitute precursors were left to incubate for 4 days at 37° C. under 5% by volume of $CO_2$, and the fraction of living cells was determined by an Alamar Blue™ test (measurement of absorbance at 570 nm and 600 nm, the quantity of living cells is the result of the ratio between these two absorbance values). It is observed that the bio-ink enables the survival of fibroblasts in the dermal substitute, and that the concentration of these living cells in the dermal substitute precursor is proportional to the concentration of living cells in the bio-ink (see FIG. 5a).

For a given cell density (in fact 100,000) the quantity of living cells was determined after 7, 10 and 14 days of culture under the incubation conditions given above. The results are shown on FIG. 5(b). It can be seen that these cells proliferate in the skin substitute over time.

After 14 days, a skin substitute stain was made by DAPI (that stains the nuclei of living cells) and propidium iodide (that stains the nuclei of dead cells). FIG. 5(c) shows the DAPI stain (grey veil and some zones stained with propidium iodide (white spots) on an optical microscopy section. FIG. 5(d) shows a control experiment on an identical sample in which the cells had been killed by a treatment with sodium dodecyl sulfate (0.5%): the white propidium iodide stain can be seen.

Example 7: Preparation of a Skin Substitute According to the Invention

A skin substitute according to the invention was prepared, and more particularly using the method illustrated on FIG. 6. FIG. 7(a) shows a cross-section through a dermis substrate obtained using the method according to the invention; this figure was obtained using an HPS (hematoxylin-phloxine-saffron) stain. FIG. 7(b) shows a cross-section through the same dermis substitute (thickness 5µ); the stain was obtained using Masson's trichrome. Fibroblast nuclei (N) and the extracellular matrix (ECM) neosynthesized by the fibroblasts can be seen in the bio-printed dermis. FIGS. 7(c), 7(d) and 7(e) show an immuno-histological marking specific for collagen I (FIG. 7(c)), collagen V (FIG. 7(d)) and fibrillin (FIG. 7(e)) in the dermis bio-printed according to the invention (in a zone overlapping the epidermis and the dermis), while FIGS. 7(f), 7(g) and 7(h) show corresponding images obtained under the same conditions on human skin, for comparison purposes (some lines on these six figures have been redrawn in dashed lines to make them more easily visible).

Vimentin and elastin were also detected (not shown on the figures).

FIGS. 7(i) and 7(j) show immuno-histological marking specific for laminin 332 (FIG. 7(i)) and collagen VII (FIG. 7(j) in the dermis bio-printed according to the invention (in another zone overlapping the epidermis and the dermis), while FIGS. 7(k) and 7(l) show corresponding images for a human skin, obtained under the same conditions, for comparison purposes.

Figure 8A:
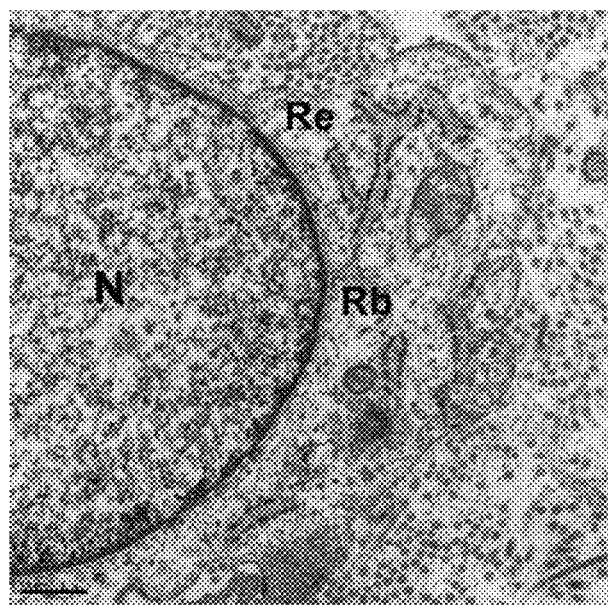
Figure 8B:
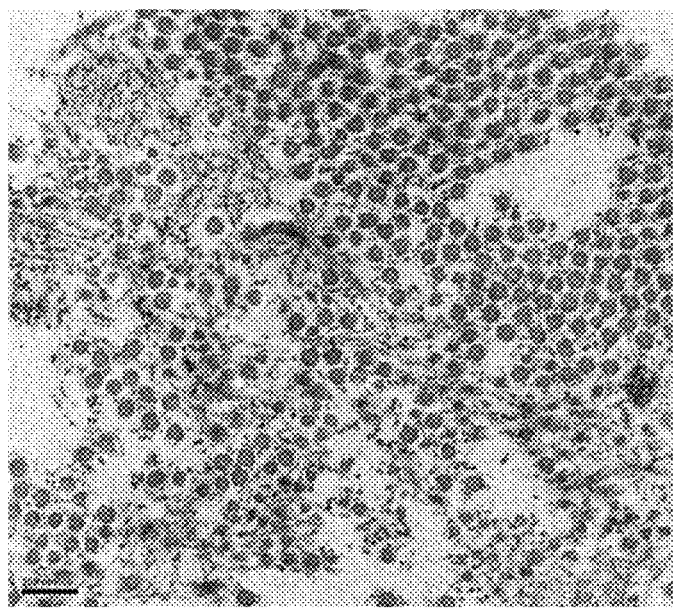

FIGS. 8(a) and 8(b) show enlargements of zones of the bioprinted dermis in FIG. 7(c), namely a fibroblast (FIG. 8(a))—the N, Re and Rb symbols denote the nucleus, the reticulum and the ribosome respectively—and neosynthesized collagen (FIG. 8(b)). In FIG. 8(a) the black bar at the left represents a length of 0.5 µm, and in FIG. 8(b) a length of 200 nm.

Figure 8C:
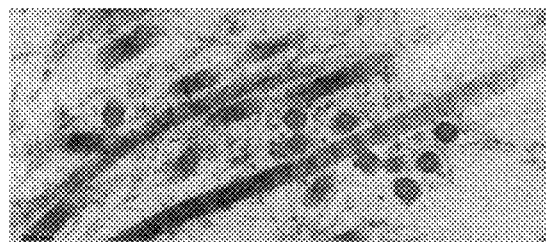
Figure 8D:
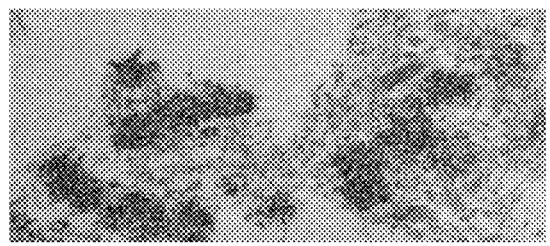

FIGS. 8(c) and 8(d) show details of FIG. 8(b), namely striated collagen (FIG. 8(c)) and a deposit of soluble elastin (FIG. 8(d)).

Figure 9:
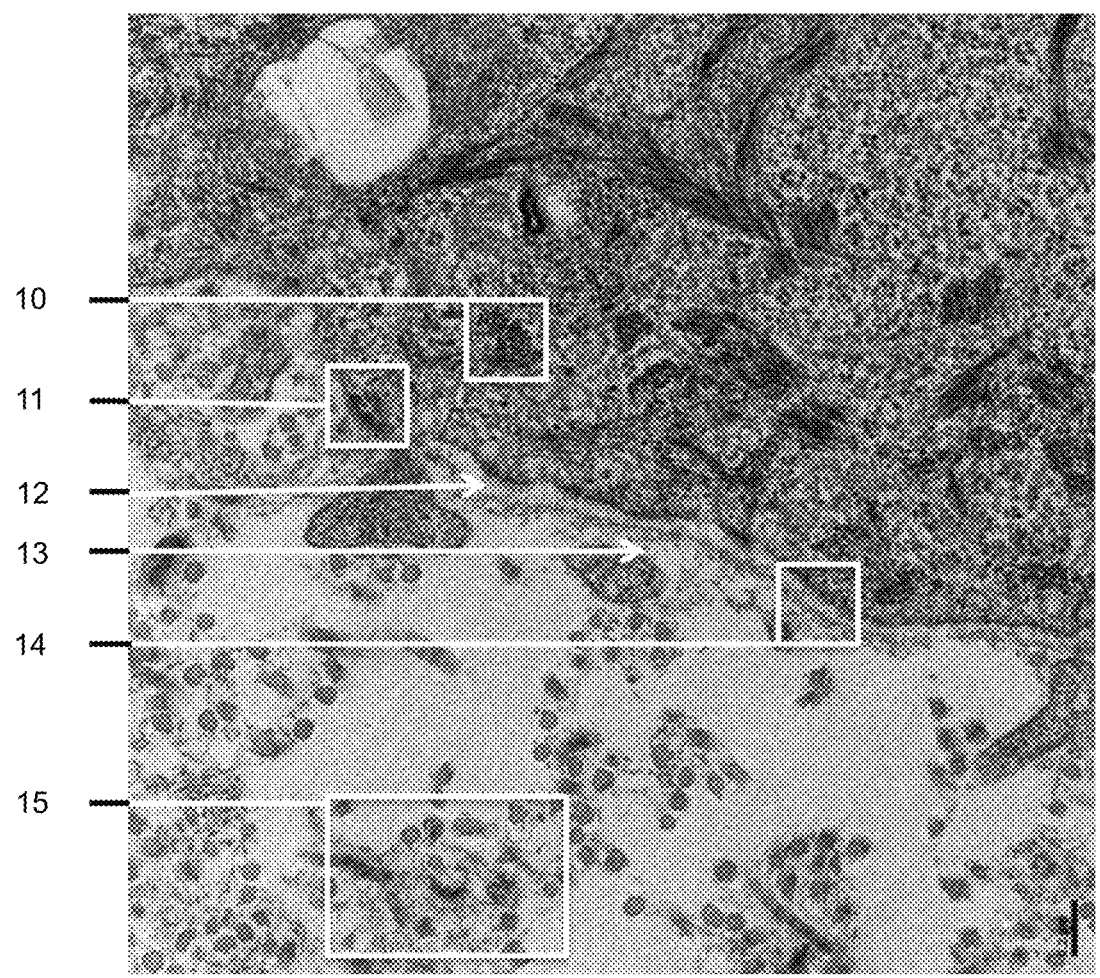

FIG. 9 shows an image of the bio-printed dermis according to the invention. The numeric marks designate ultrastructural characteristics, namely intermediate filaments of cytokeratine 10, hemidesmosome 11, the lamina *lucida* 12, the lamina *densa* 13, the anchor fibrilla 14, collagen fibers 15. The vertical bar at the bottom right represents a length of 0.2 μm.

FIGS. 10(*a*), 10(*b*) and 10(*c*) shown an immuno-histological marking specific for cytokeratine 10 (FIG. 10(*a*)), la filaggrin (FIG. 10(*b*)) and loricrin (FIG. 10(*c*)) in the dermis bio-printed according to the invention (in another zone overlapping the epidermis and the dermis), while FIGS. 10(*d*), 10(*e*) and 10(*f*) show corresponding images obtained under the same conditions on human skin, for comparison purposes.

FIG. 11(*a*) shows another ultrastructural image of the dermis substitute according to the invention; this zone shows the stratum corneum. FIGS. 11(*b*), (*c*), (*d*) and (*e*) show details, namely corneodesmosomes (FIG. 11(*b*), desmosome (FIG. 11(*c*)), keratohyaline granules (FIG. 11(*d*)), Odland lamellar bodies (FIG. 11(*e*)).

This example shows that the dermis substitute obtained using the method according to the invention is not only morphologically similar to healthy human skin, but it also expresses all biomarkers related to epidermal differentiation and proliferation (such as cytokeratine 10, filaggrin), is capable of acting as a functional barrier (see particularly the expression of loricrin), and expresses proteins that are normally found in the extracellular matrix (particularly collagen I, collagen V, fibrillin, vimentin, elastin): this illustrates the close morphological, histological and functional similarity of the dermis substitute according to the invention and human dermis.

Example 8: Body Substitute According to the Invention with Human Endothelial Cells Two bio-inks according to the invention were prepared, one containing 200,000 and the other containing 400,000 human dermal endothelial cells per milliliter. A body substitute precursor was deposited, and the viability of cells was determined after 4, 8 and 14 days of incubation with the Alamar Blue™ test described above. FIG. 12 shows the proliferation of printed endothelial cells as a function of initial cell densities.

Example 9: Body Substitute According to the Invention with Human Cornea Fibroblasts Two bio-inks were prepared according to the invention, one containing 150,000 and the other containing 200,000 human cornea fibroblasts per milliliter. A body substitute precursor was deposited, and the viability of cells was determined after 4 and 8 days of incubation with the Alamar Blue™ test described above. FIG. 13 shows the proliferation of printed cells as a function of initial cell densities.

Example 10: Body Substitute According to the Invention with Human Oral Mucosa Fibroblasts Two bio-inks were prepared according to the invention, one containing 150,000 and the other containing 200,000 human oral mucosa fibroblasts. A body substitute precursor was deposited, and the viability of cells was determined after 4 and 8 days of incubation with the Alamar Blue™ test described above. FIG. 14 shows the proliferation of printed cells as a function of initial cell densities.

Example 11: Body Substitute According to the Invention with Human Hair Follicle Dermal Papilla Fibroblasts Two bio-inks were prepared according to the invention, one containing 150,000 and the other containing 200,000 human hair follicle dermal papilla fibroblasts. A body substitute precursor was deposited, and the viability of cells was determined after 4 and 8 days of incubation with the Alamar Blue™ test described above. FIG. 15 shows the proliferation of printed cells as a function of initial cell densities.

Example 12: Bio-Inks with Various Living Cells

Four bio-inks were prepared according to the invention, one containing 100,000, the others containing 200,000, 400,000 and 600,000 adipose stem cells per milliliter of bio-ink, in a manner similar to that described in example 6, and a body substitute precursor was prepared. It is observed that the bio-ink enables the survival of adipose stem cells in the body substitute precursor, and that the concentration of these living cells in said precursor is proportional to the concentration of living cells in the bio-ink (see FIG. 16*a*).

Similarly, four bio-inks were prepared according to the invention, one containing 100,000, the others containing 200,000, 400,000 and 600,000 pre-adipocytes per milliliter of bio-ink, and a body substitute precursor was prepared. It is observed that the bio-ink enables the survival of adipose pre-adipocyte stem cells in the body substitute precursor, and that the concentration of these living cells in said precursor is proportional to the concentration of living cells in the bio-ink (see FIG. 16*b*). FIGS. 16(*c*) and 16(*d*) have been described above (in the "Figures" section).

Example 13: Fabrication of an Ear Substitute Precursor

In using the method according to the invention, a precursor of a human ear substitute with a maximum size of about 8 cm was prepared. The bio-ink was prepared with 10% (w/v) of bovine gelatin (CAS No. 9000-70-8) supplied by Sigma Aldrich (France), 0.5% (w/v) of alginate (very low viscosity, CAS No. 9005-38-3) supplied by Aesar (France), and 2% (w/v) of fibrinogen (CAS No. 9001-32-5) supplied by Sigma Aldrich (France) at a temperature of 37° C. Freshly trypsinised cells were added at a content of $1 \times 10^6$ cells per milliliter of bio-ink just before 3D printing. The homogenized bio-ink was transferred in a syringe; this filled syringe was stored at between 15° C. and 37° C. to obtain the required rheological properties. The diameter of the micropipette was 200 μm. The substrate was at ambient temperature. The untreated printed object (FIG. 17, image 1) was treated for 30 minutes in a solution (100 mM) of $CaCl_2$ in the presence of thrombin (20 U/mL, CAS No. 9002-04-4), see FIG. 17 (images B and C).

Example 14: Rheology of the Additive Deposition Method

For a bio-ink according to the invention, the viscosity was characterized using a rotational viscosity meter (AR 2000, TA Instruments company) with a cone/plane geometry (25 mm) using the shear rate scanning mode (between 0.1 and 100 $s^{-1}$) at 28° C., this temperature representing the temperature during the additive deposition. The shear rate was calculated using the equation $\tau_w = \eta \dot{\gamma}_w$ in which $\tau_w$ [Pa], $\dot{\gamma}_w$ [$s^{-1}$] and $\eta$ [Pa·s] represent the shear stress, the shear rate on the wall w of the extrusion nozzle and the viscosity of the bio-ink respectively.

The shear rate was calculated using Poiseuille's equation for a fixed bio-ink flow equal to $Q = 0.183 \text{ mm}^3 \cdot s^{-1}$ according to the equation:

$$\dot{\gamma}_w^{t,b} = \frac{3n+1}{n} \frac{Q}{\pi R_{t,b}^3}$$

The shear stress ($\tau_w$) after the nozzle inlet (t) and at the nozzle outlet (b) were determined starting from the radius (R), the shear rate ($\dot{\gamma}_w$) and the viscosity ($\eta$).

TABLE 1

Rheological characterization of the method of extrusion of a bio-ink according to the invention through a frustro-conical nozzle (length 15 mm) with a flow of Q = 0.183 mm$^3 \cdot$ s$^{-1}$.

| Parameter | Inlet (t) | Outlet (b) |
| --- | --- | --- |
| Radius [mm] | $R_t$ = 1.50 | $R_b$ = 0.20 |
| Shear rate [s$^{-1}$] | $\dot{\gamma}_w^t$ = 0.12 | $\dot{\gamma}_w^b$ = 51.78 |
| Viscosity (Pa · s) | $\eta^t$ = 94.54 | $\eta^b$ = 0.97 |
| Shear stress [Pa] | $\tau_w^t$ = 11.61 | $\tau_w^b$ = 50.48 |

It is seen that with the bio-ink according to the invention and under realistic operating conditions, the shear stress is of the order of 50 Pa. This explains the excellent cell viability observed in the previous examples, knowing that it has been reported in the state of the art that cell viability reduces for many types of cells when a shear stress of about 5,000 Pa is applied to them. Therefore the bio-ink according to the invention can be used for methods of fabricating two-dimensional or three-dimensional objects using additive deposition techniques, particularly by extrusion, using commercially available syringes and orifices.

Example 15: Body Tissue Substitute Made with a Bio-Ink Containing Pathological Cells, for Pharmacological Tests In using the method according to the invention, a skin tissue substitute is made containing pathological cells, namely fibroblasts and keratinocytes taken from patients suffering from an atopical dermatitis. This skin tissue substitute was used as an investigation model to study molecular mechanisms of this disease and to study the effect of various pharmaceutical and cosmetic preparations, particularly in topical form (cream containing active constituents) or systemic form (the active constituent being in solution in the culture medium).

The invention claimed is:

1. A method of fabricating a bio-ink, the method comprising:
 providing a first aqueous solution containing between 6% and 30% by mass of gelatin and between 0% and 5% by mass of NaCl;
 providing a second aqueous solution containing between 1% and 8% by mass of alginate and between 0% and 5% by mass of NaCl;
 providing a third aqueous solution containing between 3% and 15% by mass of fibrinogen and living cells in suspension; and
 forming a mixture is containing, about 35% to 65% by volume of the first solution, about 15% to 35% by volume of the second solution, and about 15% to 35% by volume of the third solution, such that the proportions add up to 100%,
 wherein:
 the content of NaCl is chosen such that in a combination of said first solution and said second solution, it is between 0.4% and 2% by mass, and
 said living cells are primary cells isolated from all human or animal tissue or organs.

2. The method of claim 1, wherein said living cells are isolated from connective tissue or support tissue, a muscle tissue, a nerve tissue, or an epithelia.

3. The method of claim 1, wherein said living cells are selected from the group consisting of umbilical cord blood cells, embryonic stem cells, adult stem cells, cancerous stem cells, progenitor cells, autologous cells, isograft cells, allogenic cells, xenograft cells, genetically modified cells, induced progenitor cells, transfected cells.

4. A method of fabricating a body tissue substitute, the method comprising:
 fabricating a bio-ink by:
 providing a first aqueous solution containing between 6% and 30% by mass of gelatin and between 0% and 5% by mass of NaCl,
 providing a second aqueous solution containing between 1% and 8% by mass of alginate and between 0% and 5% by mass of NaCl,
 providing a third aqueous solution containing between 3% and 15% by mass of fibrinogen and living cells in suspension, and
 forming a mixture is containing, about 35% to 65% by volume of the first solution, about 15% to 35% by volume of the second solution, and about 15% to 35% by volume of the third solution, such that the proportions add up to 100%,
 wherein:
 the content of NaCl is chosen such that in a combination of said first solution and said second solution, it is between 0.4% and 2% by mass, and
 said living cells are primary cells isolated from all human or animal tissue or organs,
 providing a polymerization solution containing between 1% and 5% by mass of calcium ions and between 10 U/mL and 30 U/mL of thrombin;
 forming an untreated printed object by heating said bio-ink to a first temperature above a gel point of said bio-ink, and then depositing said heated bio-ink on a substrate at a second temperature below the gel point of said bio-ink;
 treating said untreated printed object with said polymerization solution to consolidate said untreated printed object into a body tissue precursor;
 incubating said body tissue precursor in a cell culture medium.

5. The method of claim 4, wherein treating said untreated printed object comprises treating said untreated printed object with said polymerization solution by immersion at a third temperature that is greater than the first temperature.

6. The method of claim 4, wherein the first temperature is between 27° C. and 32° C.

7. The method of claim 6, wherein the second temperature is between 4° C. and 20° C.

8. The method of claim 7, wherein the third temperature is between 35° C. and 38° C.

9. The method of claim 4, wherein:
 said body tissue precursor comprises a skin substitute precursor, and
 said bio-ink is a suspension containing living fibroblast cells.

10. The method of claim 9, wherein said incubation is conducted at a temperature between 36° C. and 38° C.

11. The method of claim 10, wherein said incubation comprises:

a first incubation phase lasting between eight and forty days; and a second incubation phase lasting between five and ten days.

12. The method of claim 11, further comprising depositing, between the first phase and the second phase, an aqueous suspension of keratinocytes on the surface of said skin substitute precursor.

13. The method of claim 12, wherein said untreated printed object comprises a substantially flat upper surface and has a uniform distribution of fibroblasts, equal to between 0.2 and $2 \times 10^5$ fibroblasts per cm$^2$ of flat upper surface.

14. The method of claim 13, wherein the concentration of fibroblasts is between $1 \times 5 \times 10^5$ fibroblasts per cm$^3$ of bio-ink.

15. The method of claim 13, wherein the quantity of deposited keratinocytes is between 0.5 and $10 \times 10^5$ keratinocytes per cm$^2$ of said substantially flat upper surface.

16. The method of claim 4, wherein said body tissue substitute is a skin substitute formed by:

printing a hypodermis in several layers with the bio-ink containing pre-adipocytes and/or mature adipocytes, printing, on the surface of the printed hypodermis, a dermis in several layers with the bio-ink containing fibroblasts, and printing, on the surface of the printed hypodermis, an epidermis in several layers with the bio-ink containing keratinocytes.

17. The method of claim 4, wherein said body tissue substitute is a skin substitute containing:

a dermis layer comprising fibroblasts, an epidermis layer comprising keratinocytes, and a stratum corneum comprising keratinocytes.

18. The method of claim 4, wherein said body tissue substitute is a skin substitute for implantation in a body of a human subject or an animal subject.

19. A bio-ink formed by:

providing a first aqueous solution containing between 6% and 30% by mass of gelatin and between 0% and 5% by mass of NaCl;

providing a second aqueous solution containing between 1% and 8% by mass of alginate and between 0% and 5% by mass of NaCl;

providing a third aqueous solution containing between 3% and 15% by mass of fibrinogen and living cells in suspension; and forming a mixture is containing, about 35% to 65% by volume of the first solution, about 15% to 35% by volume of the second solution, and about 15% to 35% by volume of the third solution, such that the proportions add up to 100%, wherein:

the content of NaCl is chosen such that in a combination of said first solution and said second solution, it is between 0.4% and 2% by mass, and said living cells are primary cells isolated from all human or animal tissue or organs.

20. The method of claim 1, wherein said living cells are selected from a group formed from stem cells, differentiated cells, and somatic cells.

21. The method of claim 1, wherein said living cells are selected from a group formed from cells originating from connective tissue or support tissue, muscle tissue, nerve tissue, and epithelial tissue.

22. The method of claim 1, wherein said living cells are selected from a group formed from mesodermal cells, ectodermal cells, and endodermal cells.

23. The method of claim 1, wherein said living cells are selected from a group formed from lymphocytes, myeloid cells, granulocytes, basophil granulocytes, eosinophil granulocytes, neutrophil granulocytes, hyper segmented neutrophils, monocytes, macrophages, reticulocytes, mast cells, thrombocytes, megakaryocytes, dendritic cells, thyroid cells, thyroid epithelial cells, parafollicular cells, parathyroid cells, parathyroid chief cells, oxyphil cells, adrenal cells, chromaffin cells, pineal cells, glial cells, glioblasts, astrocytes, oligodendrocytes, microglial cells, magnocellular neurosecretion cells, stellar cells, and Boettcher cells.

24. The method of claim 1, wherein said living cells are selected from a group formed from pituitary cells, gonadotrophs, corticotrophs, thyrotrophs, somatotrophs, lactotrophs, and lung cells.

25. The method of claim 1, wherein said living cells are selected from a group formed from alveolar macrophages, myocardiocytes, pericytes, gastric cells, parietal cells, goblet cells, Paneth cells, G cells, D cells, ECL cells, I cells, K cells, S cells, enteroendocrine cells, enterochromaffin cells, APUD cells, liver cells, bone cells, cartilage cells, hair cells, skin cells, muscle cells, tendon cells, kidney cells, sperms, sertoli cells, Leydig cells, and ovocytes.

* * * * *